US011229528B2

(12) United States Patent
Dewey et al.

(10) Patent No.: US 11,229,528 B2
(45) Date of Patent: Jan. 25, 2022

(54) SPINAL IMPLANT

(71) Applicant: Warsaw Orthopedic, Inc., Warsaw, IN (US)

(72) Inventors: Jonathan M. Dewey, Memphis, TN (US); Anthony J. Melkent, Germantown, TN (US); William D. Armstrong, Memphis, TN (US); Roy K. Lim, Germantown, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 72 days.

(21) Appl. No.: 16/739,295

(22) Filed: Jan. 10, 2020

(65) Prior Publication Data

US 2020/0146838 A1 May 14, 2020

Related U.S. Application Data

(63) Continuation of application No. 15/818,395, filed on Nov. 20, 2017, now Pat. No. 10,575,962.

(51) Int. Cl.
*A61F 2/44* (2006.01)
*A61F 2/30* (2006.01)

(52) U.S. Cl.
CPC ............ *A61F 2/447* (2013.01); *A61F 2/4425* (2013.01); *A61F 2002/30538* (2013.01); *A61F 2002/30556* (2013.01); *A61F 2002/30579* (2013.01); *A61F 2002/30843* (2013.01); *A61F 2002/30845* (2013.01)

(58) Field of Classification Search
CPC ...... A61F 2/4455; A61F 2/446; A61F 2/4465; A61F 2/447
See application file for complete search history.

(56) References Cited

U.S. PATENT DOCUMENTS

| 2006/0217806 A1* | 9/2006 | Peterman | ................ A61F 2/447 623/17.11 |
| 2006/0217807 A1* | 9/2006 | Peterman | ............... A61F 2/4611 623/17.11 |
| 2008/0015695 A1* | 1/2008 | Eckman | ................ A61F 2/4455 623/17.11 |
| 2010/0198263 A1 | 8/2010 | Siegal et al. | |

(Continued)

OTHER PUBLICATIONS

International Search Report and Written Opinion PCT/2018/061166 dated Mar. 5, 2019, the US counterpart application; 10 pages.

(Continued)

*Primary Examiner* — Julianna N Harvey

(57) ABSTRACT

A spinal implant for insertion into a disc space between an upper vertebral body and a lower vertebral body is provided. The spinal implant includes an upper first end plate portion and a lower second end plate portion each extending from at least adjacent a proximal end to a distal end of the spinal implant. The spinal implant is configured to facilitate insertion into the disc space and inhibit withdrawal from the disc space. To the end, the leading end of the spinal implant can be configured to facilitate ease of insertion into the disc space, and an upper surface and a lower surface of the upper first end plant portion and the lower second end plate portion, respectively, can be provided with depressions or dimples forming ridges and points therebetween to inhibit withdrawal from the disc space.

23 Claims, 25 Drawing Sheets

(56) References Cited

U.S. PATENT DOCUMENTS

| | | |
|---|---|---|
| 2015/0112442 A1 | 4/2015 | Foley |
| 2015/0374508 A1 | 12/2015 | Sandul |
| 2016/0120660 A1 | 5/2016 | Melkent et al. |
| 2016/0374826 A1 | 12/2016 | Palmatier et al. |
| 2017/0105844 A1 | 4/2017 | Kuyler et al. |
| 2017/0112630 A1* | 4/2017 | Kuyler .................. A61F 2/4455 |
| 2017/0189200 A1 | 7/2017 | Miller et al. |

OTHER PUBLICATIONS

Extended European Search Report for EP Application No. EP18878911.9 dated Jul. 28, 2021.

* cited by examiner

SPINAL IMPLANT

CROSS-REFERENCE TO RELATED APPLICATION

This application is a continuation of U.S. patent application Ser. No. 15/818,395 filed Nov. 20, 2017, and the disclosure of the above-identified application is hereby incorporated by reference in its entirety.

BACKGROUND OF THE INVENTION

Field of the Invention

The present invention relates to a spinal implant for insertion into a disc space between adjacent vertebral bodies. More particularly, the present invention relates to a spinal implant configured to facilitate insertion into the disc space and inhibit withdrawal from the disc space. More specifically, the present invention relates to an expandable spinal implant including a leading end configured to facilitate ease of insertion into the disc space, and/or having upper and lower surfaces with depressions or dimples forming ridges and points therebetween for inhibiting withdrawal from the disc space.

Description of the Prior Art

Some of the degenerative conditions that affect the spine of a patient may be so severe as to require surgical intervention. Oftentimes, the degenerative conditions are such that a spinal implant is required to restore or enhance spinal lordosis. Such spinal implants are insertable into a disc space between two adjacent vertebral bodies of adjacent vertebrae of the patient. Push-in expandable spinal implants have previously been used for correcting the degenerative conditions that affect the spine. However, there is a need for a push-in expandable spinal implant including a leading end configured to facilitate ease of insertion into the disc space, and having upper and lower surfaces configured to inhibit withdrawal from the disc space. The leading end can include a nose portion configured to facilitate initial insertion into the disc space, and the upper and lower surfaces can include depressions or dimples forming ridges and points therebetween for inhibiting withdrawal from the disc space.

SUMMARY OF THE INVENTION

The present invention in one preferred embodiment contemplates a spinal implant for insertion into a disc space between an upper vertebral body and a lower vertebral body, the spinal implant including a proximal end, an opposite distal end, a length between the proximal end and the distal end, and a mid-longitudinal axis extending along the length through the proximal end and the distal end, an upper first end plate portion extending from at least adjacent the proximal end to the distal end, an upper surface of the upper first end plate portion being configured to engage at least a portion of an end plate of the upper vertebral body when the spinal implant is inserted into the disc space between the upper and lower vertebral bodies, a lower second end plate portion extending from at least adjacent the proximal end to the distal end, a lower surface of the lower second end plate portion being configured to engage at least a portion of an end plate of the lower vertebral body when the spinal implant is inserted into the disc space between the upper and lower vertebral bodies, and the upper first end plate portion including a first lateral surface, a second lateral surface, and a first leading end portion, each of the first lateral surface and the second lateral surface of the upper first end plate portion being opposite from one another and extending from at least adjacent the proximal end to the first leading end portion of the upper first end plate portion, the first leading end portion of the upper first end plate portion including a first nose portion and a first angled surface, the first nose portion being configured to facilitate initial insertion of the spinal implant into the disc space, the lower second end plate portion including a third lateral surface, a fourth lateral surface, and a second leading end portion, each of the third lateral surface and the fourth lateral surface of the lower second end plate portion being opposite from one another and extending from at least adjacent to the proximal end to the second leading end portion of the lower second end plate portion, the second leading end portion of the lower second end plate portion including a second nose portion and a second angled surface, the second nose portion being configured to facilitate initial insertion of the spinal implant into the disc space, and the upper first end plate portion and the lower second end plate portion each being pivotally moveable with respect to one another to facilitate movement of the spinal implant between an unexpanded configuration and an expanded configuration; where a first plane bisecting the spinal implant into an upper portion and a lower portion extends through the proximal end, the distal end, and along the mid-longitudinal axis, the first and second nose portions being at least in part arcuate in planes adjacent and parallel to the first plane, where a second plane perpendicular to the first plane and transverse to the mid-longitudinal axis bisects each of the first nose portion and the second nose portion, the first nose portion and the second nose portion each approximating a half-circle in the second plane, and where the first leading end portion and the second leading portion each extend from a third plane perpendicular to the second plane to the distal end, distances between the first plane and the first angled surface of the first leading end portion in the second plane decrease from the third plane to the distal end, and distances between the first plane and the second angled surface of the second leading end portion in the second plane decrease from the third plane to the distal end.

The present invention in another preferred embodiment contemplates a spinal implant for insertion into a disc space between an upper vertebral body and a lower vertebral body, the spinal implant including a proximal end, an opposite distal end, a length between the proximal end and the distal end, and a mid-longitudinal axis extending along the length through the proximal end and the distal end, an upper first end plate portion extending from at least adjacent the proximal end to the distal end, at least a portion of an upper surface of the upper first end plate portion being configured to engage at least a portion of an end plate of the upper vertebral body when the spinal implant is inserted into the disc space between the upper and lower vertebral bodies, a lower second end plate portion extending from at least adjacent the proximal end to the distal end, at least a portion of a lower surface of the lower second end plate portion being configured to engage at least a portion of an end plate of the lower vertebral body when the spinal implant is inserted into the disc space between the upper and lower vertebral bodies, and the upper first end plate portion including a first leading end portion, the first leading end portion of the upper first end plate portion including a first nose portion, a first angled surface, a second angled surface, and a third angled surface, the first nose portion being configured to facilitate initial insertion of the spinal implant into the disc space, the second angled surface being positioned on one side of the second angled surface and extending from the nose portion to the upper surface, and the third angled surface being positioned on the other side of the third angled surface and extending from the nose portion to the upper surface, the lower second end plate portion including a second leading end portion, the second leading end portion of the lower second end plate portion including a second nose portion, a fourth angled surface, a fifth angled surface, and a sixth angled surface, the second nose portion being configured to facilitate initial insertion of the spinal implant into the disc space, the fifth angled surface being positioned on one side of the fourth angled surface and extending from the nose portion to the lower surface, and the sixth angled surface being position on the other side of the fourth angled surface and extending from the nose portion to the lower portion, and the upper first end plate portion and the lower second end plate portion each being pivotally moveable with respect to one another to facilitate movement of the spinal implant between an unexpanded configuration and an expanded configuration; where a first plane bisecting the spinal implant into an upper portion and a lower portion extends through the proximal end, the distal end, and along the mid-longitudinal axis, the first and second nose portions being at least in part arcuate in planes adjacent and parallel to the first plane, where a second plane perpendicular to the first plane and transverse to the mid-longitudinal axis bisects each of the first nose portion and the second nose portion, the first nose portion and the second nose portion each approximating a half-circle in the second plane, and wherein the first leading end portion and the second leading portion each extend from a third plane perpendicular to the second plane to the distal end, distances between the first plane and the first angled surface of the first leading end portion in the second plane decrease from the third plane to the distal end, and distances between the first plane and the second angled surface of the second leading end portion in the second plane decrease from the third plane to the distal end.

The present invention in yet another preferred embodiment contemplates a spinal implant for insertion into a disc space between an upper vertebral body and a lower vertebral body, the spinal implant including a proximal end and an opposite distal end, an upper first end plate portion extending from at least adjacent the proximal end to the distal end, an upper surface of the upper first end plate portion being configured to engage at least a portion of an end plate of the upper vertebral body when the spinal implant is inserted into the disc space between the upper and lower vertebral bodies, a lower second end plate portion extending from at least adjacent the proximal end to the distal end, a lower surface of the lower second end plate portion being configured to engage at least a portion of an end plate of the lower vertebral body when the spinal implant is inserted into the disc space between the upper and lower vertebral bodies, and the upper first end plate portion including a first lateral surface and a second lateral surface, each of the first lateral surface and the second lateral surface of the upper first end plate portion being opposite from one another and extending from at least adjacent the proximal end to at least adjacent the distal end, the lower second end plate portion including a third lateral surface and a fourth lateral surface, each of the third lateral surface and the fourth lateral surface of the lower second end plate portion being opposite from one another and extending from at least adjacent to the proximal end to at least adjacent the distal end, an upper first extension portion formed contiguously with the upper first end plate, the upper first extension portion having a first leading end including a first nose portion and a first angled surface, at least the first nose portion being positioned on an opposite side of a first plane extending along the second side surface and the fourth side surface than a second plane positioned between the first side surface and the second side surface, a lower first extension portion formed contiguously with the lower first end plate, the lower first extension portion having a second leading end including a second nose portion and a second angled surface, at least the second nose portion being positioned on an opposite side of a third plane extending along the second side surface and the fourth side surface than a fourth plane positioned between the third side surface and the fourth side surface, and the upper first end plate portion and the lower second end plate portion each being pivotally moveable with respect to one another to facilitate movement of the spinal implant between an unexpanded configuration and an expanded configuration; where a fifth plane bisecting the spinal implant into an upper portion and a lower portion extends through the proximal end, the distal end, and along the mid-longitudinal axis, the first and second nose portions being at least in part arcuate in planes adjacent and parallel to the fifth plane, where a sixth plane perpendicular to the fifth plane and transverse to the mid-longitudinal axis bisects each of the first nose portion and the second nose portion, the first nose portion and the second nose portion each approximating a half-circle in the sixth plane, and where the first leading end portion and the second leading portion each extend from a seventh plane perpendicular to the second plane to the distal end, distances between the fifth plane and the first angled surface of the first leading end portion in the sixth plane decrease from the seventh plane to the distal end, and distances between the fifth plane and the second angled surface of the second leading end portion in the sixth plane decrease from the seventh plane to the distal end.

BRIEF DESCRIPTION OF THE DRAWINGS

FIG. 2A is enlarged portion of the expandable spinal implant of FIG. 1;

DETAILED DESCRIPTION OF THE PREFERRED EMBODIMENT

A spinal implant according to a first preferred embodiment of the present invention is generally indicated by the numeral 10 in FIGS. 1-8. The spinal implant 10 is expandable and is configured for insertion in a disc space between an upper first vertebral body and a lower second vertebral body adjacent to one another. As discussed below, the spinal implant 10 can include features facilitating insertion into the disc space, can include features inhibiting withdrawal thereof from the disc space, and can include features facilitating fusion between the first and second vertebral bodies. The spinal implant 10 includes many of the features facilitating expansion thereof similar to that of a spinal implant disclosed in U.S. Ser. No. 14/885,472, U.S. Publication No. 2017/0105844, which is herein incorporated by reference in its entirety.

Figure 7:
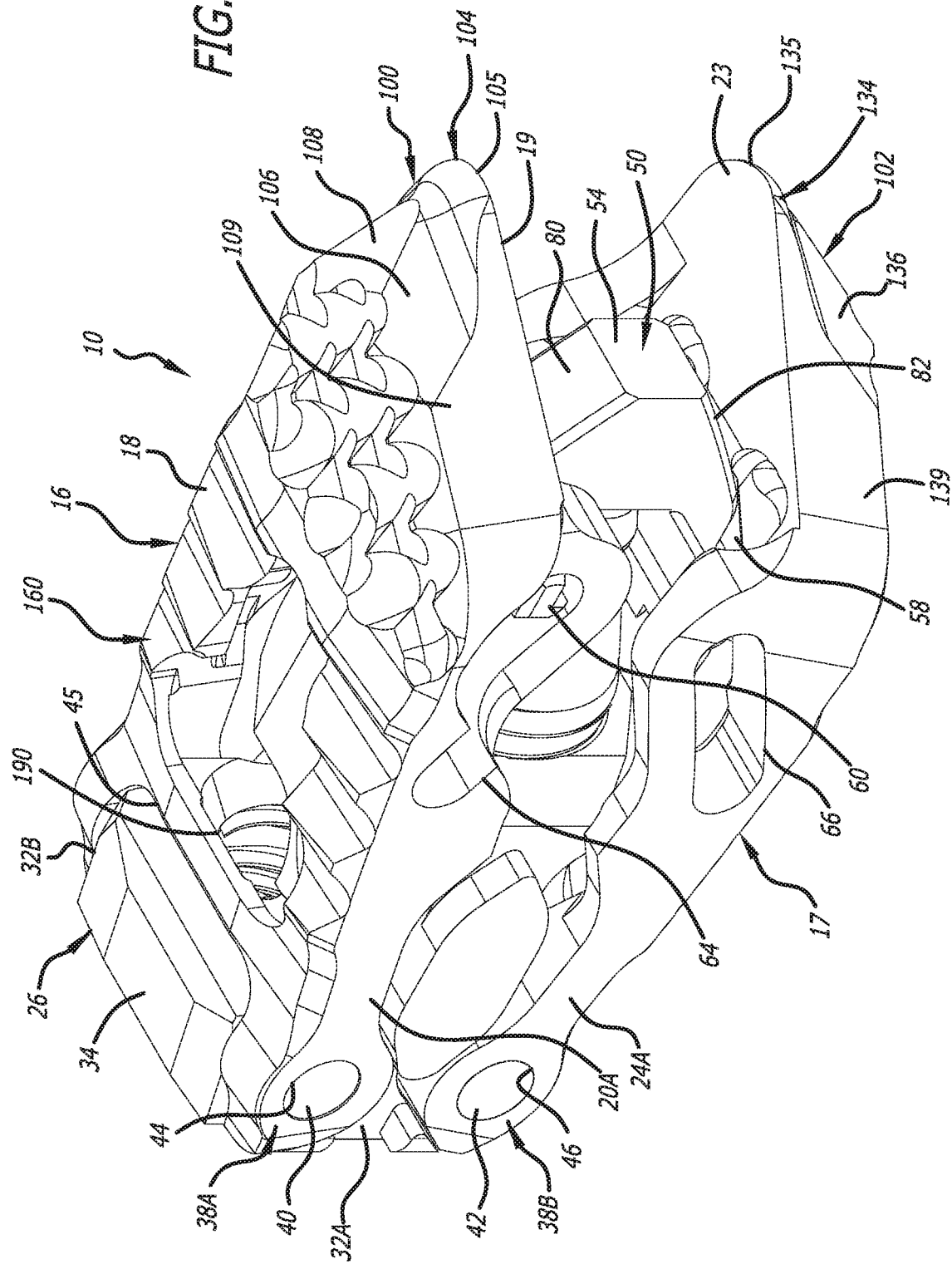
FIG. 7 is a top front perspective view of the expandable spinal implant of FIG. 1 in an expanded configuration.
Figure 8:
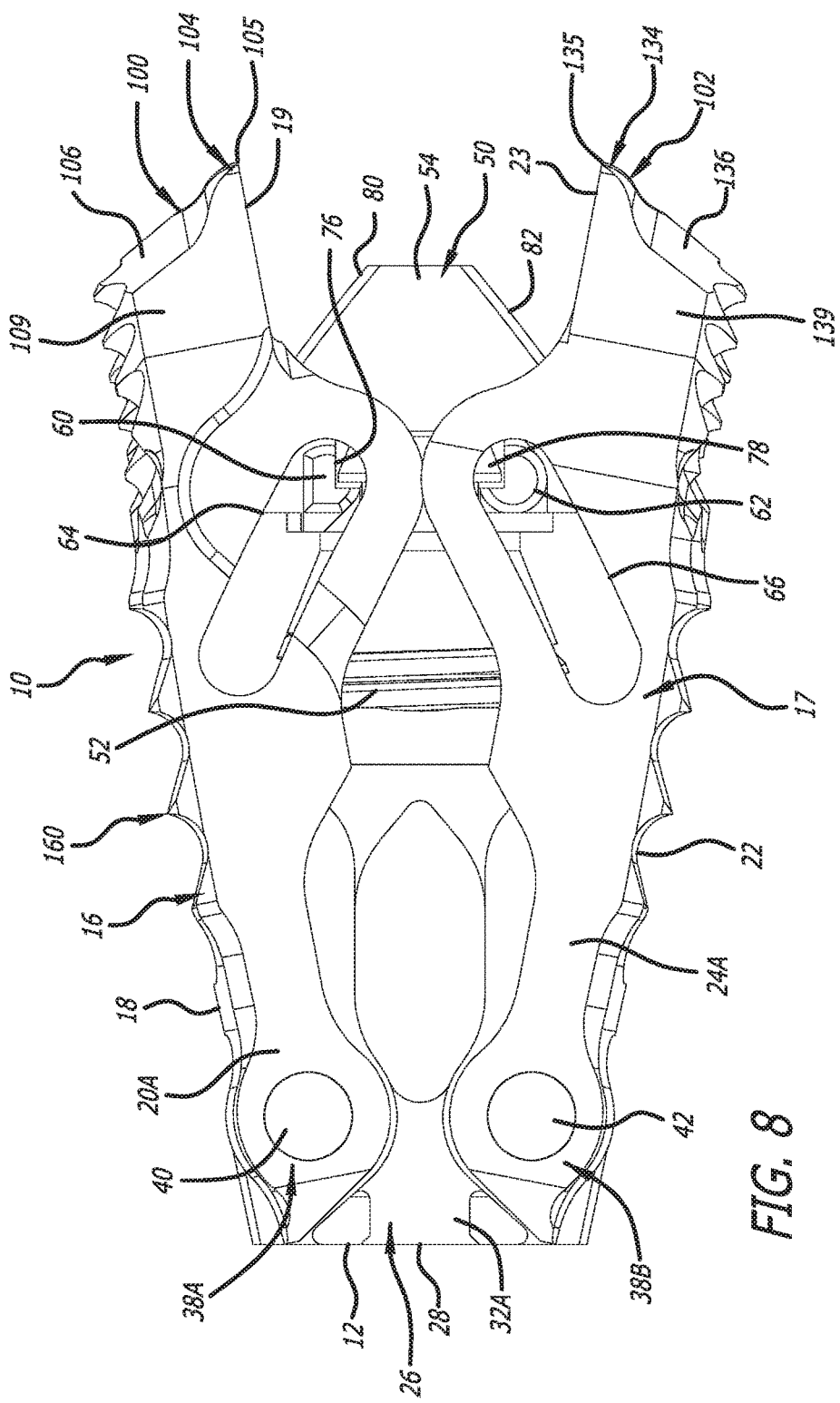
FIG. 8 is a side elevational view of the expandable spinal implant of FIG. 1 in the expanded configuration.

As depicted in FIGS. 1-8, the spinal implant 10 is also moveable between an unexpanded first configuration and an expanded second configuration (FIGS. 7 and 8). As such, the spinal implant 10 can be inserted in the unexpanded first configuration into the disc space, and thereafter, the spinal implant 10 can be expanded from the unexpanded first configuration to the expanded second configuration. The expansion of the spinal implant 10 can be used in correcting various spinal disorders.

To illustrate, such expansion can be used to facilitate increasing or restoring an appropriate lordotic orientation of the first and second vertebral bodies with respect to one another. For example, the spinal implant 10 can be configured for insertion into the disc space from a direct posterior (sometimes referred to as PLIF procedures) in pairs or singularly and then be expanded to impart and/or augment a lordotic curve of the spine. Furthermore, the spinal implant 10 can also be configured for use in oblique, postero-lateral procedures and/or transforaminal lumbar interbody fusions (sometimes referred to as TLIF procedures), and be used to impart and/or restore both a lordotic angle as well as align the spine in the coronal plane (so as to treat a scoliotic curvature, for example).

As depicted in FIGS. 1-8, the spinal implant 10 includes a proximal end 12, an opposite distal end 14, a length L (FIG. 6) extending between the proximal end 12 and the distal end 14, and a mid-longitudinal axis A extending through the proximal end 12 and the distal end 14. The spinal implant 10 includes an upper first end plate 16 and a lower second end plate 17. As discussed below, at least one of the upper first end plate 16 and the lower second end plate 17 is moveable. For example, one or both of the upper first end plate 16 and the lower second end plate 17 are moveable to move the spinal implant 10 between the unexpanded first configuration and the expanded second configuration.

The upper first end plate 16 includes an upper surface 18, an interior surface 19, and first and second side surfaces 20A and 20B, and the lower second end plate includes a lower surface 22, an interior surface 23, and first and second side surfaces 24A and 24B.

In addition to the upper first end plate 16 and the lower second end plate 17, the spinal implant 10, as depicted in FIGS. 1-8, includes a frame member 26 to which the upper first end plate 16 and the lower second end plate 17 are attached. The frame member 26 includes a first end portion 28, a second end portion 30, a first lateral side wall portion 32A, a second lateral side wall portion 32B, an upper wall portion 34, and a lower wall portion 36. The first end portion 28 of the frame member 26 is provided at the proximal end 12 of the spinal implant 10, and the second end portion 30 is spaced from the first end portion 28 by the first lateral side wall portion 32A, the second lateral side wall portion 32B, the upper wall portion 34, and the lower wall portion 36. The second end portion 30 is positioned proximate the midpoint of the length L of the spinal implant 10.

The upper first end plate 16 and the lower second end plate 17 can be pivotally attached to the first end portion 28 of the frame member 26 via hinge mechanisms 38A and 38B. The hinge mechanism 38A includes upper posts 40 provided on the first end portion 28 and complementary structures provided on the upper first end plate 16, and the hinge mechanism 38B includes lower posts 42 provided on the first end portion 28 and complementary structures provided on the lower second end plate 17. As such, the upper first end plate 16 is engaged to the first end portion 28 using the upper posts 40 and the lower second end plate 17 is engaged to the first end portion 28 using the lower posts 42. To facilitate such engagement, the hinge mechanism 38A includes complementary structures such as apertures 44 and cut-out portions 45 provided on the upper first end plate 16, and the hinge mechanism 38B includes complementary structures such as apertures 46 and cut-out portions 47 provided on the lower second end plate 17.

As depicted in FIGS. 1-4 and 6-8, one of the upper posts 40 is received in one of the apertures 44, and the other of the upper posts 40 is received in the other of the apertures 44, and one of the lower posts 42 is received in one of the apertures 46, and the other of the lower posts 42 is received in the other of the apertures 46. The interaction of the upper posts 40 with the apertures 44 and the interaction of the lower posts 42 with the apertures 46 afford pivotal movement of the upper first end plate 16 and the lower second end plate 17, respectively. Furthermore, the cut-out portions 45 and 47 avoid interference of the upper first end plate 16 and the lower second end plate 17 with the first end portion 28, and hence, afford pivotal movement of the first end portion 28 with the upper first end plate 16 and the lower second end plate 17, respectively.

As depicted in FIGS. 7 and 8, the spinal implant 10 also includes an expansion mechanism 50 facilitating controlled movement of at least one of the upper first end plate 16 and the lower second end plate 17 relative to the frame member 26. More specifically, the expansion mechanism 50 can control pivotal movement of each of the upper first end plate 16 and the lower second end plate 17 with respect to the frame member 26. As such, the expansion mechanism 50 facilitates movement of the spinal implant 10 between the unexpanded first configuration and the expanded second configuration.

The expansion mechanism 50 can include a plug 52 moveable with respect to the frame member 26, a head portion 54 operatively connected to the plug 52, a first ramp (not shown) provided on the upper first end plate 16, a second ramp 58 provided on the lower second end plate 17, upper posts 60 and lower posts 62, a first set of slots 64 provided on the upper first end plate 16, and a second set of slots 66 provided on the lower second end plate 17.

The plug 52 includes threads 70 provided thereon, and the threads 70 operatively engage complementary threads 72 provided at least in part along an aperture 74 extending through the frame member 26. The aperture 74 extends through and between the first end portion 28 and the second end portion 30. In doing so, the aperture 74 extends between the first and second lateral side wall portions 32A and 32B, the upper portion 34, and the lower portion 36. The plug 52 can be moved inwardly and outwardly with respect to the aperture 74 (and the frame portion 26) adjacent the second end portion 30 by interaction between the threads 70 and 72 via rotation of the plug 52.

The head portion 54 includes a notch 76 for receiving a post 78 formed on the plug 52. The interaction between the notch 76 and the post 78 attaches the plug 52 to the head portion 54, while also affording rotation of the post 78 in the notch 76. As such, movement of the plug 52 inwardly and outwardly with respect to the frame member 26 moves the head portion 54 toward and away from, respectively, the frame member 26. Furthermore, rotation of the post 78 in the notch 76 averts the application of rotational forces to the head portion 54. As such, the head portion 54 can be moved toward and away from the frame member 26 via rotational movement of the plug 52 without itself being rotated.

The head portion 54 includes an upper first ramp 80 and a lower second ramp 82. The upper first ramp 80 is provided to engage the first ramp provided on the upper first end plate 16, and the lower second ramp 82 is provided to engage the second ramp 58 provided on the lower second end plate 17. Movement of the head portion 54 away from the frame member 26 (and toward the distal end 14) causes contact with and movement of the upper first ramp 80 along the first ramp portion and the lower second ramp 82 along the second ramp portion 58. As depicted in FIG. 7, the upper first ramp 80, the lower second ramp 82, the first ramp portion, and the second ramp portion 58 are angled such that, when the upper first ramp 80 contacts the first ramp portion, the lower second ramp 82 contacts the second ramp portion 58, and the head portion 54 is moved toward the distal end 14, the upper first end plate 16 and the lower second end plate 17 are forced to pivot away from one another and the frame member 26. As such, the interaction between the upper first ramp 80 and the first ramp portion, and the interaction between the lower second ramp 82 and the second ramp portion 58 facilitates the movement of the spinal implant 10 from the unexpanded configuration to the expanded configuration.

The interaction between the upper posts 60 and the first set of slots 64 and between the lower posts 62 and the second set of slots 66 also facilitates the movement of the spinal implant 10 from the unexpanded configuration to the expanded configuration. The upper posts 60 are provided on an upper portion and on either lateral side of the head portion 54, and the lower posts 62 are provided on a lower portion and on either lateral side of the head portion 54. One of the upper posts 60 is received in one slot of the first set of slots 64, the other of the upper posts 60 is received in the other slot of the first set of slots 64, one of the lower posts 62 is received in one slot of the second set of slots 66, and the other of the lower posts 62 is received in the other slot of the second set of slots 66. As depicted in FIGS. 1-4 and 6-8, the first set of slots 64 and the second set of slots 66 are angled such that, when the upper posts 60 are received in the first set of slots 64, the lower posts 62 are received in the second set of slots 66, and the head portion 54 is moved toward the distal end 14, the upper first end plate 16 and the lower second end plate 17 are forced to pivot away from one another and the frame member 26.

After insertion of the spinal implant 10 into the disc space between the first and second vertebral bodies, the plug 52 can be rotated to move the head portion 54 toward the distal end 14. The above-discussed interactions caused by the movement of the head portion 54 force the upper first end plate 16 and the lower second end plate 17 apart from one another to move the spinal implant 10 from the unexpanded configuration to the expanded configuration.

The spinal implant 10 can also be configured to facilitate insertion into the disc space. For example, the upper first end plate 16 and the lower second end plate 17 at the proximal end 12 can be configured for ease of insertion into the disc space. To that end, the upper first end plate 16 includes a leading end portion 100 and the lower second end plate 17 includes a leading end portion 102 configured to facilitate insertion into the disc space. As discussed below, both of the leading end portions 100 and 102 include features facilitating ease of insertion into the disc space.

The leading end portion 100 of the upper first end plate 16 includes a nose portion 104, a first angled surface 106, a second angled surface 107, a third angled surface 108 disposed between the first and second angled surfaces 106 and 107, and a front side surface 109. The first, second, and third angled surfaces 106, 107, and 108 are substantially planar. The nose portion 104 is provided at the distal end 14 of the spinal implant 10, and extends rearwardly from a leading edge 105 formed at the intersection of the nose portion 104 and the interior surface 19.

The first angled surface 106 extends rearwardly from the nose portion 104 between a first edge 110 and a second edge 112, and terminates at a third edge 114. Furthermore, the second angled surface 107 extends rearwardly from the nose portion 104 between a fourth edge 116 and a fifth edge 118, and terminates at a sixth edge 120. The third angled surface 108 extends rearwardly from a curved seventh edge 122 provided adjacent the nose portion 104 between the second edge 112 and the fifth edge 118, and terminates at an eighth edge 124. The front side surface 109 extends from the first side surface 20A to the first edge 110.

The front side surface 109 can be substantially vertical. The first angled surface 106 is angled at approximately 160±20 degrees with respect to the front side surface 109, the first angled surface 106 is angled at approximately 120±20 degrees with respect to the third angled surface 108, and the second angled surface 107 is angled at approximately 120±20 degrees with respect to the third angled surface 108.

The first angled surface 106 is bordered by the nose portion 104, the first edge 110, the second edge 112, and the third edge 114. The first edge 110 is partially formed at the intersection of the front side surface 109 with the first angled surface 106, the second edge 112 is formed at the intersection of the first angled surface 106 with the third angled surface 108, and the third edge 114 is formed at the intersection of the first angled surface 106 with the upper surface 18 of the upper first end plate 16.

The second angled surface 107 is bordered by the nose portion 104, the fourth edge 116, the fifth edge 118, and the sixth edge 120. The fourth edge 116 is partially formed at the intersection of the side surface 20B with the second angled surface 107, the fifth edge 118 is formed at the intersection of the second angled surface 107 with the third angled surface 108, and the sixth edge 120 is formed at the intersection of the second angled surface 107 with the upper surface 18 of the upper first end plate 16.

Figure 1:
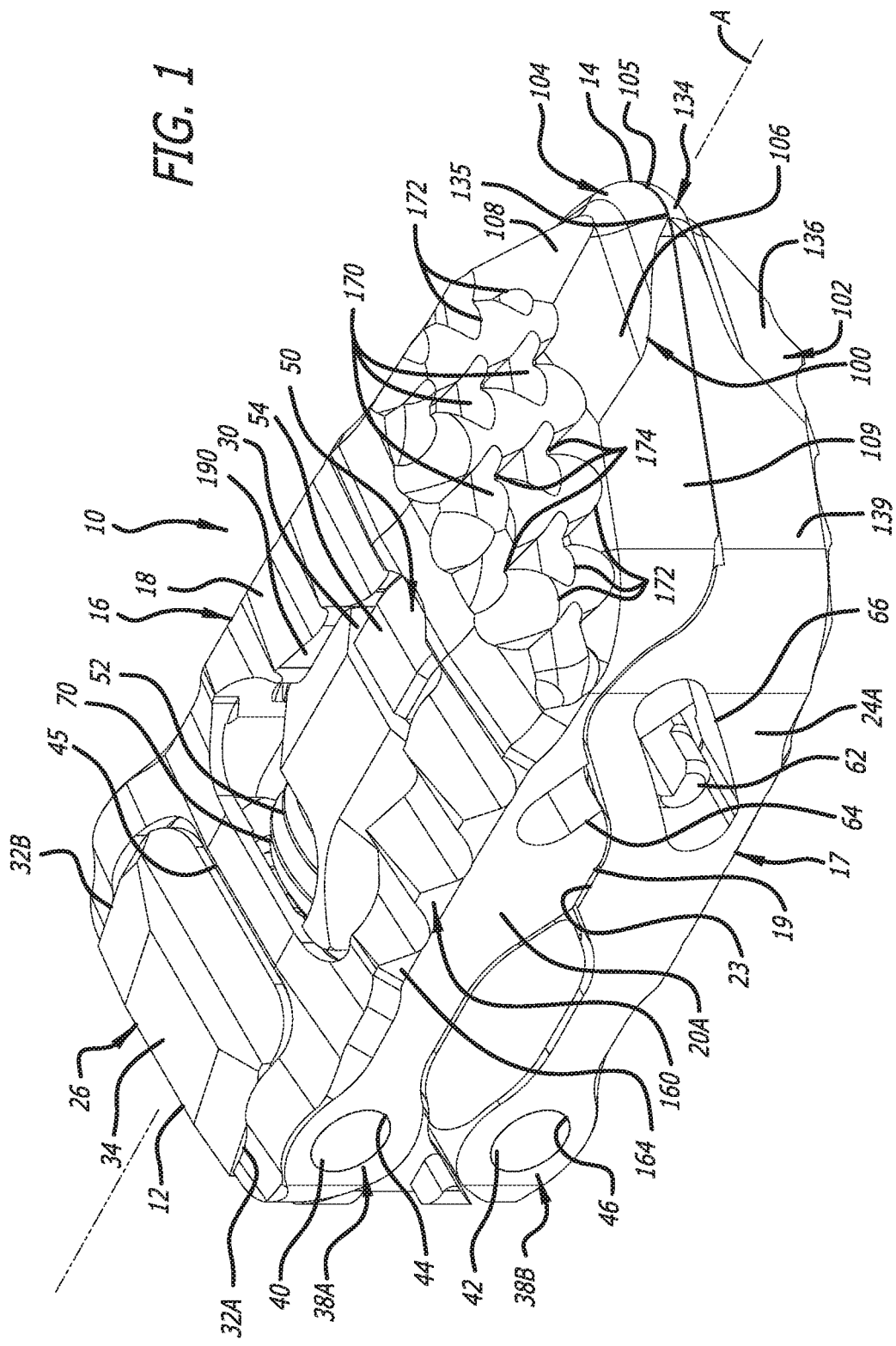
FIG. 1 is a top side perspective view of an expandable spinal implant in an unexpanded configuration.
Figure 2:
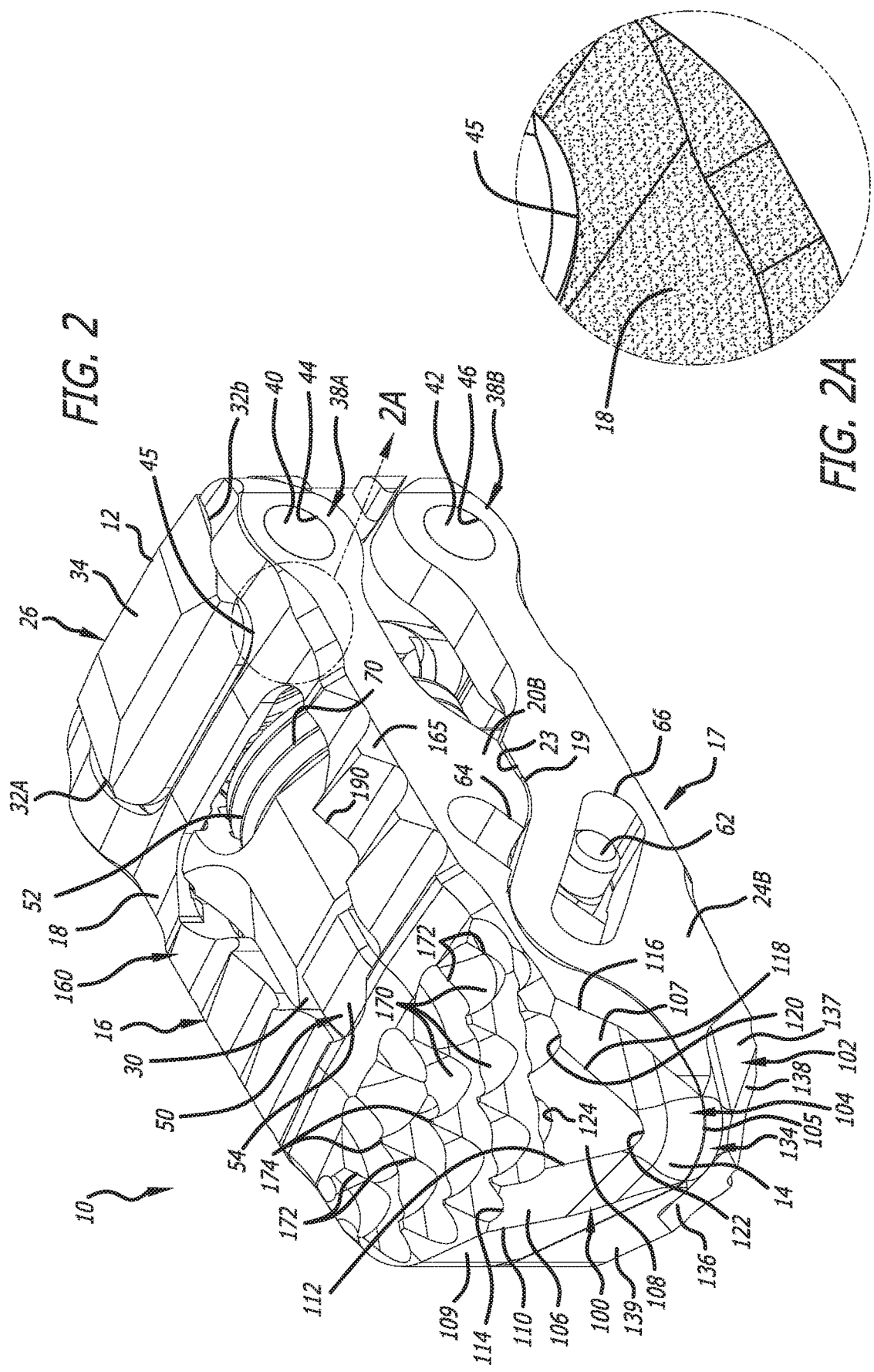
FIG. 2 is top front perspective view of the expandable spinal implant of FIG. 1 in the unexpanded configuration.
Figure 3:
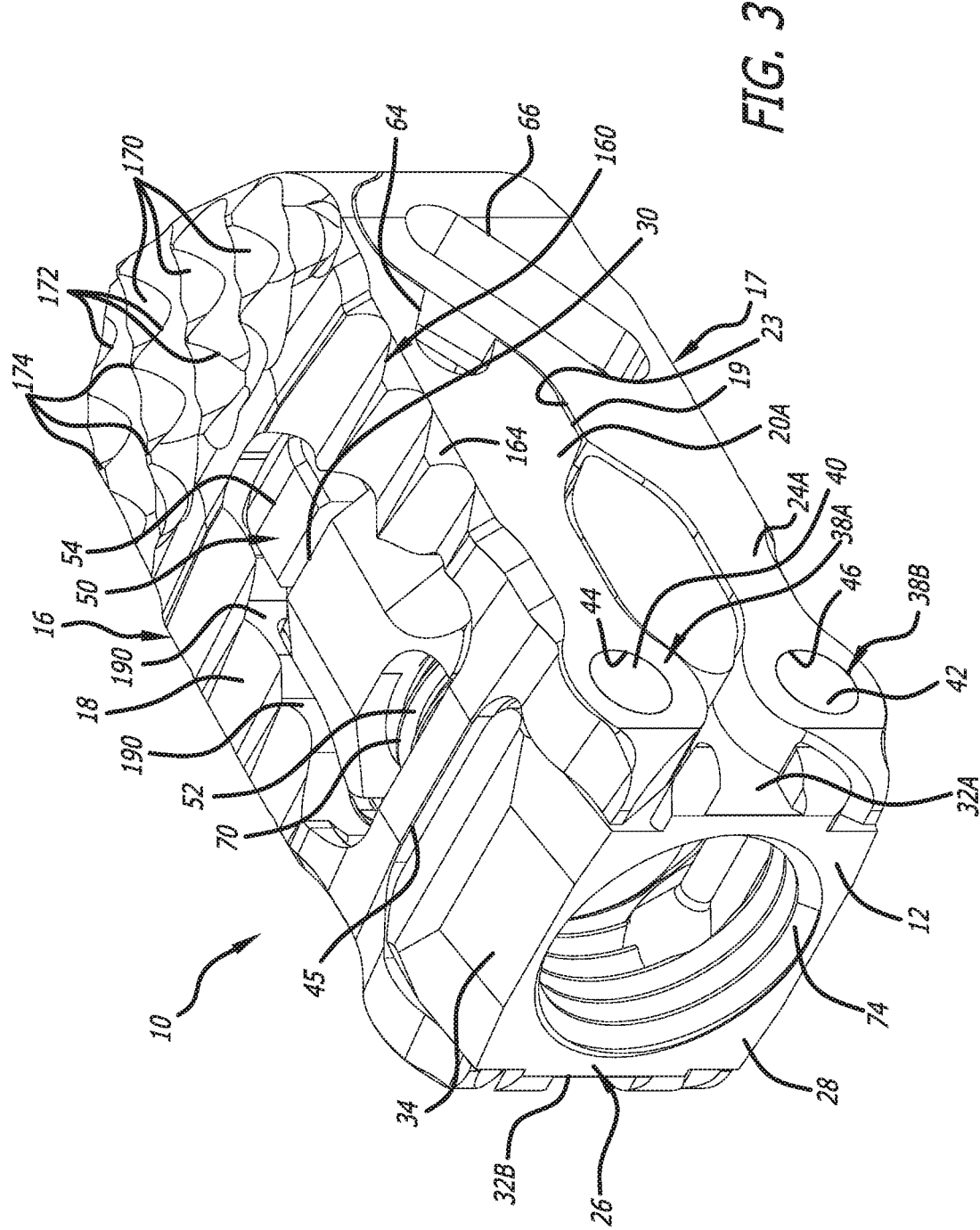
FIG. 3 is a top rear perspective view of the expandable spinal implant of FIG. 1 in the unexpanded configuration.
Figure 5:
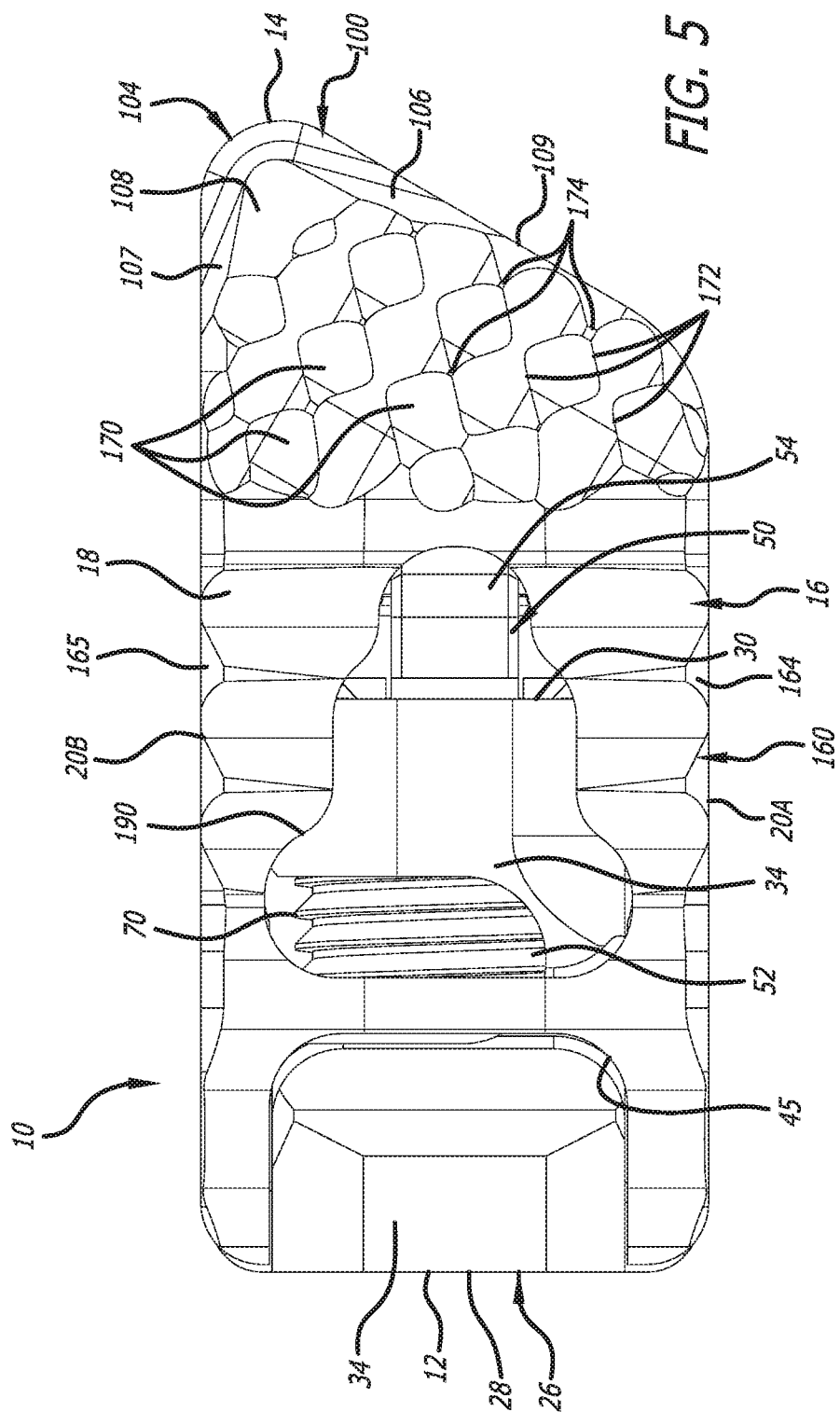
FIG. 5 is a top plan view of the expandable spinal implant of FIG. 1 in the unexpanded configuration.
Figure 6:
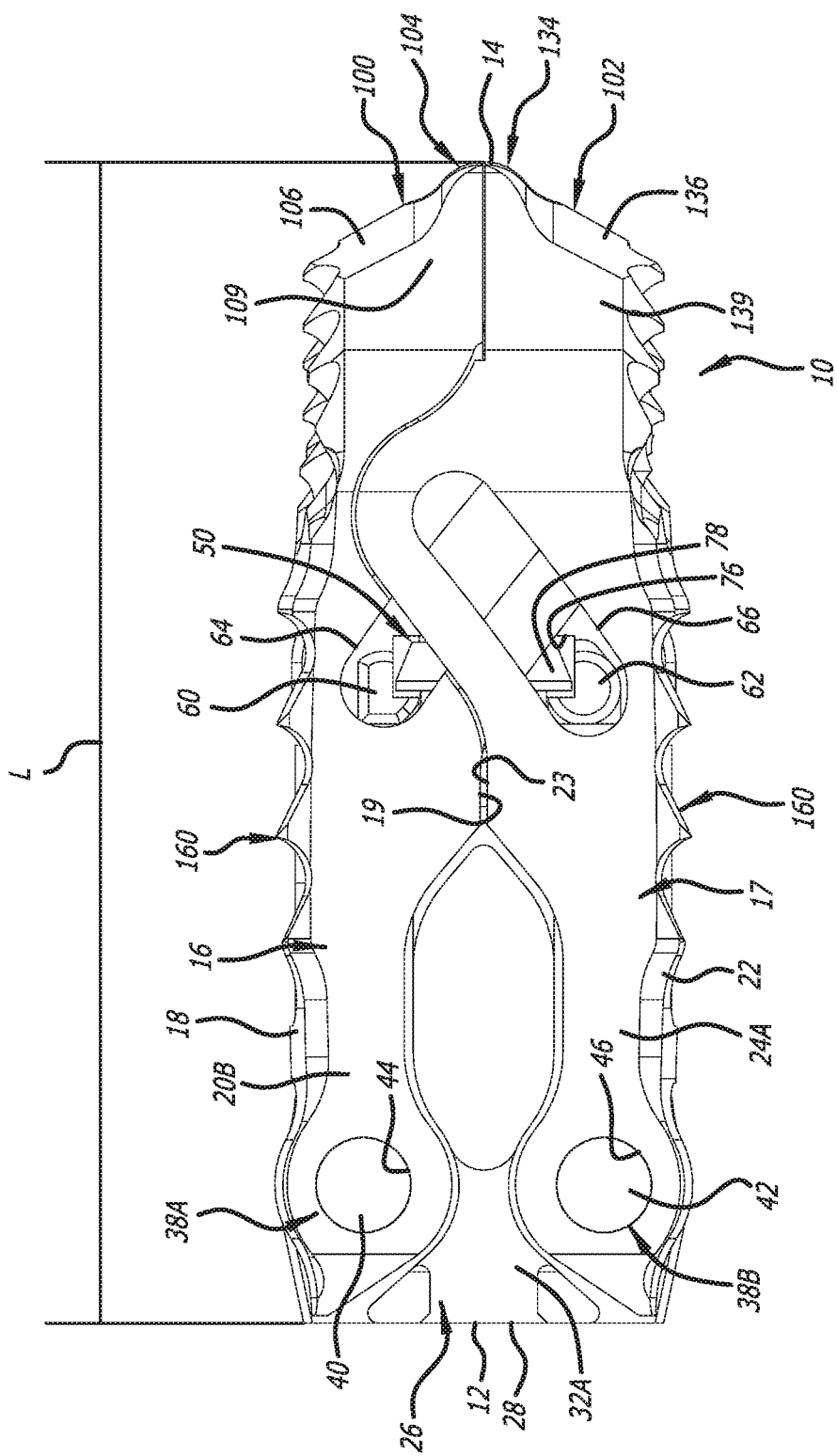
FIG. 6 is a side elevational view of the expandable spinal implant of FIG. 1 in the unexpanded configuration.

As depicted in FIGS. 1, 2, and 5, the nose portion 104 protrudes outwardly from at least the first and second angled surfaces 106 and 107. The nose portion 104 is bordered by the leading edge 105, the first edge 110, the fourth edge 116, the seventh edge 122, the first angled surface 106, and the second angled surface 107, where the nose portion 104 smoothly transitions into the first and second angled surfaces 106 and 107. The smooth transitions between the nose portion 104 and the first angled surface 106 and between the nose portion 104 and the second angled surface 107 forms concavities.

On the surface thereof, the nose portion 104 can include a first arcuate portion in a first plane extending along the mid-longitudinal axis A and in which the leading edge 105 resides when the spinal implant 10 is in the unexpanded configuration. The first arcuate portion can approximate a half-circle in the first plane. The nose portion 104 includes further arcuate portions in planes parallel to the first plane that are stacked upwardly from the first plane.

On the surface thereof, the nose portion 104 also can include a second arcuate portion in a second plane perpendicular to the first plane that extends generally rearwardly from the leading edge 105 and that bisects the third angled surface 108. The second arcuate portion can approximate a quarter-circle in the second plane. The nose portion 104 includes further arcuate portions in planes parallel to the second plane and are on either side thereof.

The leading end portion 102 of the lower second end plate 17 includes a nose portion 134, a first angled surface 136, a second angled surface 137, a third angled surface 138 disposed between the first and second angled surfaces 136 and 137, and a front side surface 139. The first, second, and third angled surfaces 136, 137, and 138 are substantially planar.

The nose portion 134 is provided at the distal end 14 of the spinal implant 10, and extends rearwardly from a leading edge 135 formed at the intersection of the nose portion 104 and the interior surface 23. The nose portion 134 smoothly transitions into the first and second angled surfaces 136 and 137.

The first angled surface 136 extends rearwardly from the nose portion 134 between a first edge 140 and a second edge 142, and terminates at a third edge 144. Furthermore, the second angled surface 137 extends rearwardly from the nose portion 134 between a fourth edge 146 and a fifth edge 148, and terminates at a sixth edge 150. The third angled surface 138 extends rearwardly from a curved seventh edge 152 provided adjacent the nose portion 134 between the second edge 142 and the fifth edge 148, and terminates at an eighth edge 154. The front side surface 139 extends from the first side surface 24A to the first edge 140.

The front side surface 139 can be substantially vertical. The first angled surface 136 is angled at approximately 160±20 degrees with respect to the front side surface 139, the first angled surface 136 is angled at approximately 120±20 degrees with respect to the third angled surface 138, and the second angled surface 137 is angled at approximately 120±20 degrees with respect to the third angled surface 138.

The first angled surface 136 is bordered by the nose portion 134, the first edge 140, the second edge 142, and the third edge 144. The first edge 140 is formed at the intersection of the front side surface 139 with the first angled surface 136, the second edge 142 is formed at the intersection of the first angled surface 136 with the third angled surface 138, and the third edge 144 is formed at the intersection of the first angled surface 136 with the lower surface 22 of the lower second end plate 17.

The second angled surface 137 is bordered by the nose portion 134, the fourth edge 146, the fifth edge 148, and the sixth edge 150. The fourth edge 146 is formed at the intersection of the side surface 24B with the second angled surface 137, and the fifth edge 148 is formed at the intersection of the second angled surface 137 with the third angled surface 138, and the sixth edge 150 is formed at the intersection of the second angled surface 137 with the lower surface 22 of the lower second end plate 17.

Figure 4:
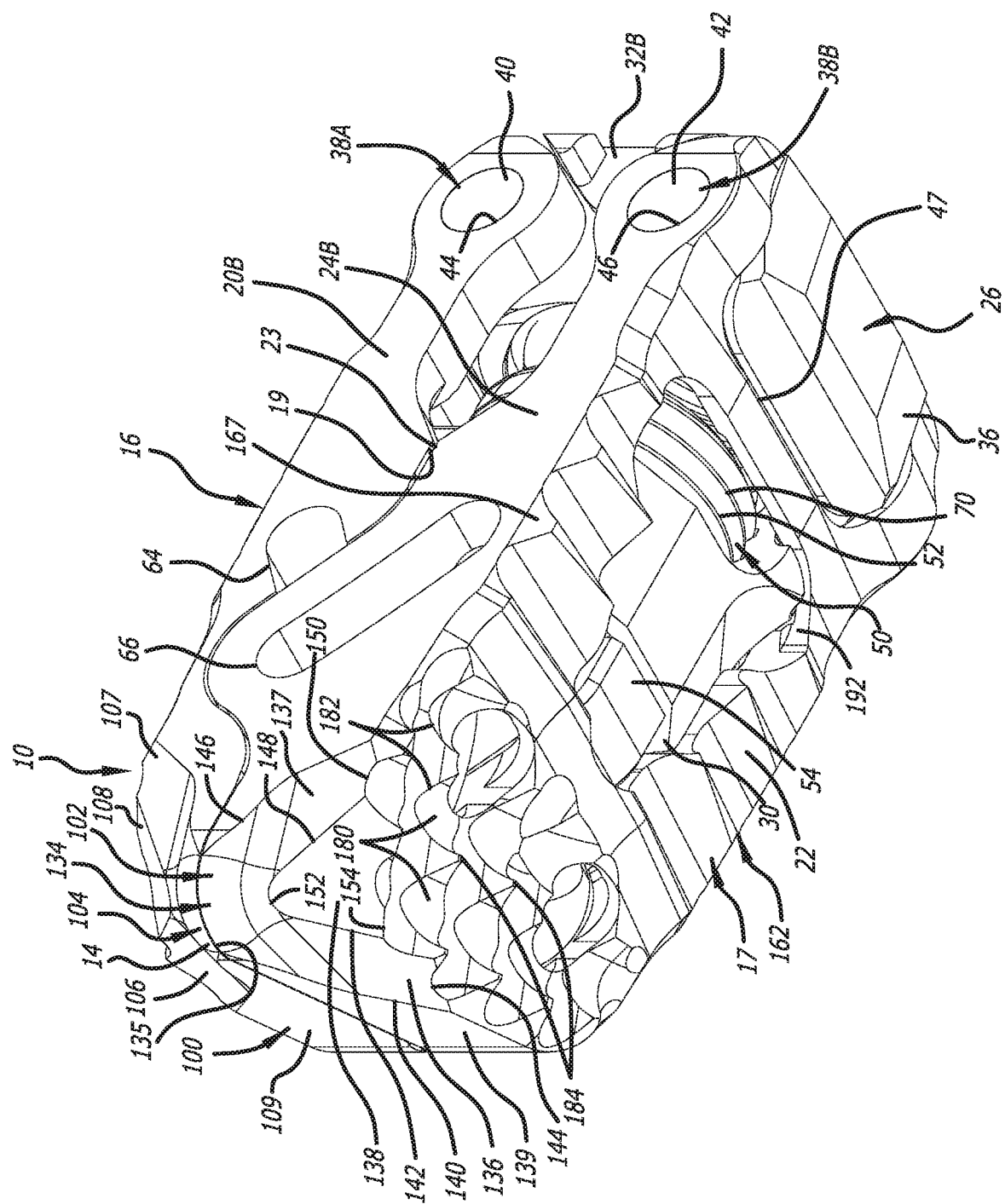
FIG. 4 is a bottom front perspective view of the expandable spinal implant of FIG. 1 in the unexpanded configuration.

As depicted in FIG. 4, the nose portion 134 protrudes outwardly from at least the first and second angled surfaces 136 and 137. The nose portion 134 is bordered by the leading edge 105, the first edge 140, the fourth edge 146, the seventh edge 152, the first angled surface 136, and the second angled surface 137, where the nose portion 134 smoothly transitions into the first and second angled surfaces 136 and 137. The smooth transitions between the nose portion 134 and the first angled surface 136 and between the nose portion 104 and the second angled surface 137 forms concavities.

On the surface thereof, the nose portion 134 can include a first arcuate portion in a third plane extending along the mid-longitudinal axis A and in which the leading edge 135 resides when the spinal implant 10 is in the unexpanded configuration. The first arcuate portion can approximate a half-circle in the third plane. The nose portion 134 includes further arcuate portions in planes parallel to the third plane that are stacked upwardly from the third plane.

On the surface thereof, the nose portion 134 also can include a second arcuate portion in a fourth plane perpendicular to the second plane that extends generally rearwardly from the leading edge 135 and that bisects the third angled surface 138. The second arcuate portion can approximate a quarter-circle in the second plane. The nose portion 134 includes further arcuate portions in planes to the second plane and are on either side thereof.

The features of the leading end portions 100 and 102 at the distal end 14 of the spinal implant 10 facilitate insertion thereof into the disc space between first and second vertebral bodies. For example, when the spinal implant 10 is in the unexpanded configuration, the leading end portions 100 and 102 ease the insertion of the spinal implant 10 into the disc space. To illustrate, during insertion of the spinal implant 10 in the unexpanded configuration, the nose portions 104 and 134 are first inserted into the disc space. In doing so, depending on the degree of spinal deformity, the nose portions 104 and 134 may or may not contact either of the first and second vertebral bodies during initial insertion. After initial insertion, the nose portion 104 is contacted to the first vertebral body and the nose portion 134 is contacted to the second vertebral body. Thereafter, the remaining portions of the leading end portions 100 and 102 are contacted to the first and second vertebral bodies, respectively. To illustrate, during further insertion of the spinal implant 10 in the unexpanded configuration into the disc space, the first vertebral body slides along portions of the first angled surface 106, the second angled surface 107, and/or the third angled surface 108, and the second vertebral body slides along portions of the first angled surface 136, the second angled surface 137, and/or the third angled surface 138. Given the angled configurations of the first angled surfaces 106 and 136, the second angled surfaces 107 and 137, and the third angled surfaces 108 and 138, the leading end portions 100 and 102 together act as a wedge to spread apart the first and second vertebral bodies to facilitate insertion of the spinal implant 10 into the disc space.

An insertion instrument (not shown) can be used to manipulate the spinal implant 10 during insertion thereof into the disc space. For example, the insertion instrument could be removably attached to the proximal end 12 of the spinal implant 10. Thereafter, the spinal implant 10 could be manipulated into position, as discussed above, in the disc space between the first and second vertebral bodies.

The upper first end plate 16 and the lower second end plate 17 can be configured to facilitate placement of the spinal implant 10 in the disc space, inhibit withdrawal of the spinal implant 10 once positioned in the disc space, and promote interbody fusion between the first and second vertebral bodies.

To facilitate placement of the spinal implant 10, the upper surface 18 of the upper first end plate 16 and the lower surface 22 of the lower second end plate 17 can include surface features facilitating slidable movement of the spinal implant 10 within the disc space. For example, the upper surface 18 can include a first set of ratchets 160 and the lower surface 22 can include a second set of ratchets 162. The first and second sets of ratchets 160 and 162 are oriented to facilitate movement of the spinal implant in a forward direction oriented along the mid-longitudinal axis A of the spinal implant 10, and to resist movement in a rearward direction oriented along the mid-longitudinal axis A. In addition to or in place of the first and second sets of ratchets 160 and 162, the upper surface 18 and the lower surface 22 can include additional surface protrusions (including, for example, pyramids, ridges, spikes, and/or teeth) configured to facilitate slidable movement of the spinal implant 10 within the disc space. Furthermore, in addition to or in place of the first and second set of ratchets 160 and 162, the upper surface 18 and the lower surface 22 can include roughened surfaces, as depicted in FIG. 2A, to facilitate bone ingrowth and aid in boney attachment and fixation of the upper surface 18 and the lower surface 22 to the endplates of the first and second vertebral bodies, respectively. Such roughened surfaces for facilitating bone ingrowth could be created by mechanical means, grit blast, plasma spray, acid etch, and/or 3D-printing to name a few possibilities.

Additionally, the first set of ratchets 160 can include chamfers 164 adjacent the first side surface 20A, and can include chamfers 165 adjacent the second side surface 20B. Furthermore, the second set of ratchets 162 can include chamfers 166 adjacent the first side surface 24A, and can include chamfers 167 adjacent the second side surface 24B. The chamfers 164, 165, 166, and 167 facilitate movement of the spinal implant 10 in directions transverse to the mid-longitudinal axis A, and reduce abrasion to adjacent tissues during insertion.

In addition to the first and second sets of ratchets 160 and 162 resisting movement in a rearward direction oriented along the mid-longitudinal axis A, the upper surface 18 and the lower surface 22 can include additional surface features resisting movement of the spinal implant 10. For example, the upper surface 18 can include various depressions or dimples 170 that form ridges 172 and points 174 therebetween. Furthermore, the lower surface 22 can include various depressions or dimples 180 that form ridges 182 and points 184 therebetween. After placing the spinal implant 10 in the disc space, the ridges 172 and 182 and the points 174 and 184 can engage the endplates of the first and second vertebral bodies to resist movement of the spinal implant 10. Moreover, the bone from the endplates of the first and second vertebral bodies can grow into the various depressions 170 and 180 which enhances the resistance of the spinal implant 10 movement.

To promote interbody fusion between the first and second vertebral bodies, the upper first end plate 16 and the lower second end plate 17 can include apertures therethrough that allow for bone growth through the spinal implant between the first and second vertebral bodies. For example, the upper first end plate 16 can include an aperture 190 extending therethrough between the upper surface 18 and the interior surface 19, and the lower second end plate 17 can include an aperture 190 extending therethrough between the lower surface 22 and the interior surface 23. Bone ingrowth into the first and second apertures 190 and 192 from the first and second vertebral bodies facilitates interbody fusion.

Figure 9:
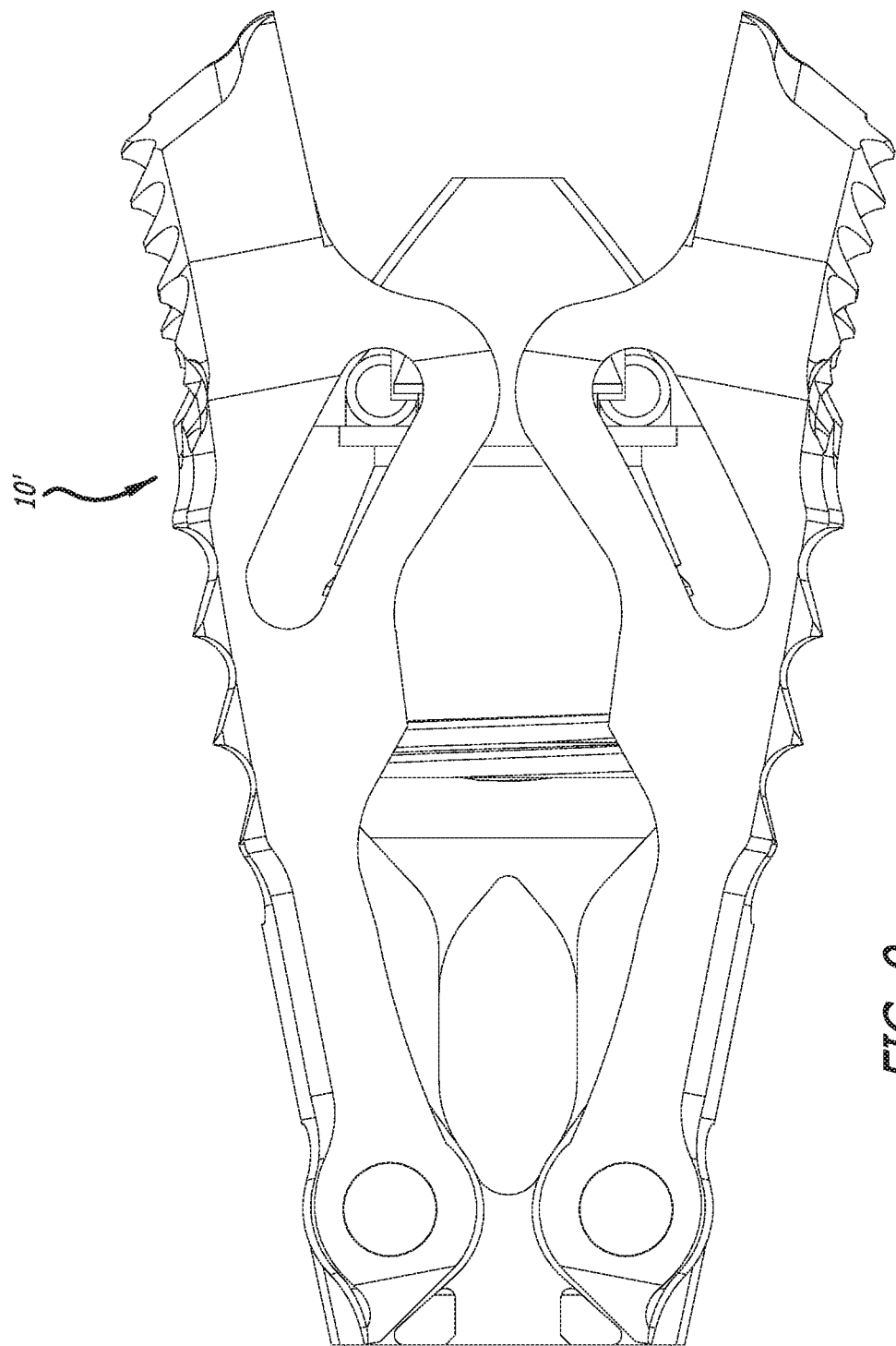
FIG. 9 is a side elevational view of an expandable spinal implant similar to that of FIG. 1 in an expanded configuration and having a first larger size.
Figure 10:
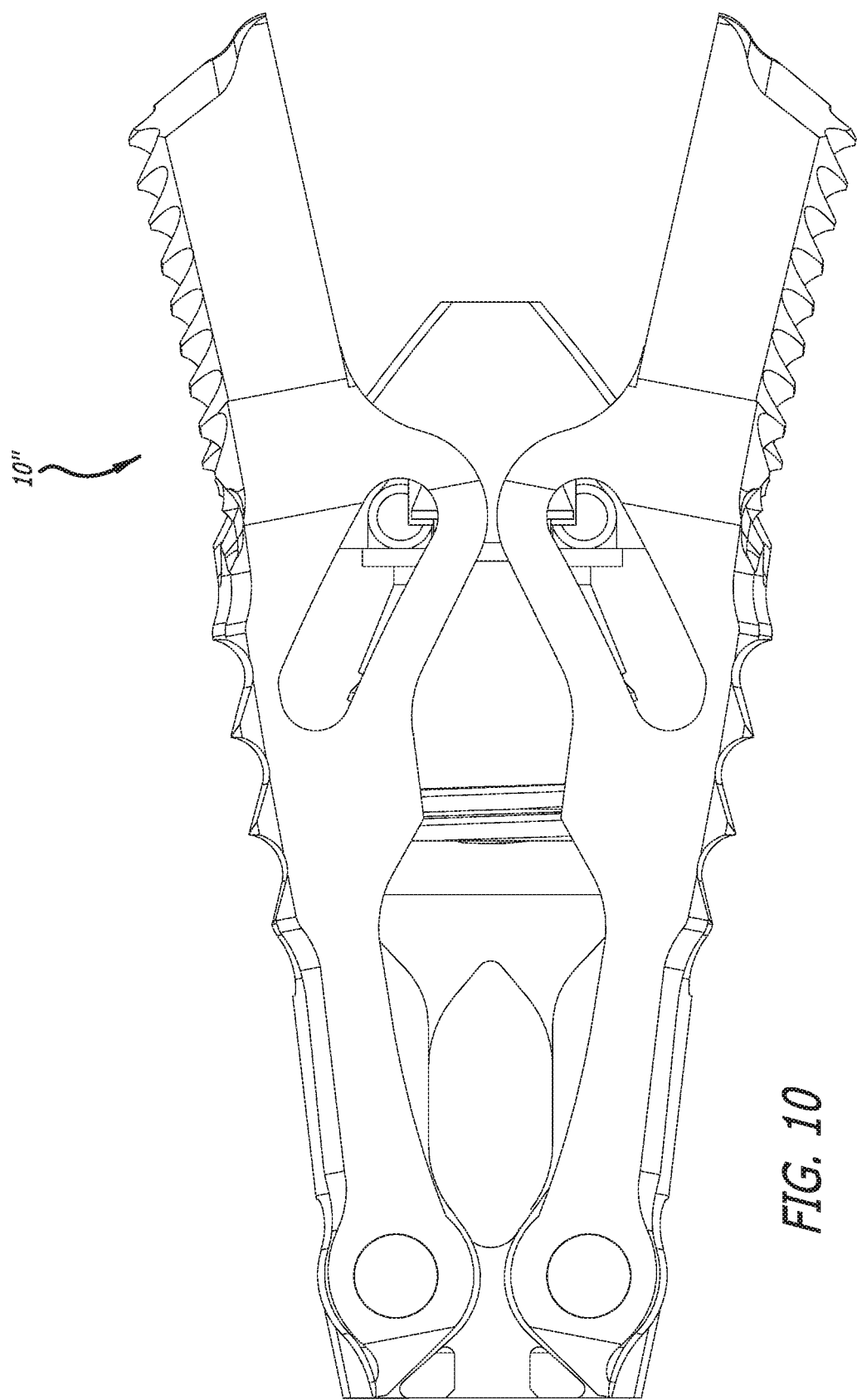
FIG. 10 is a side elevational view of an expandable spinal implant similar to that of FIG. 1 in an expanded configuration and having a second larger size.
Figure 11:
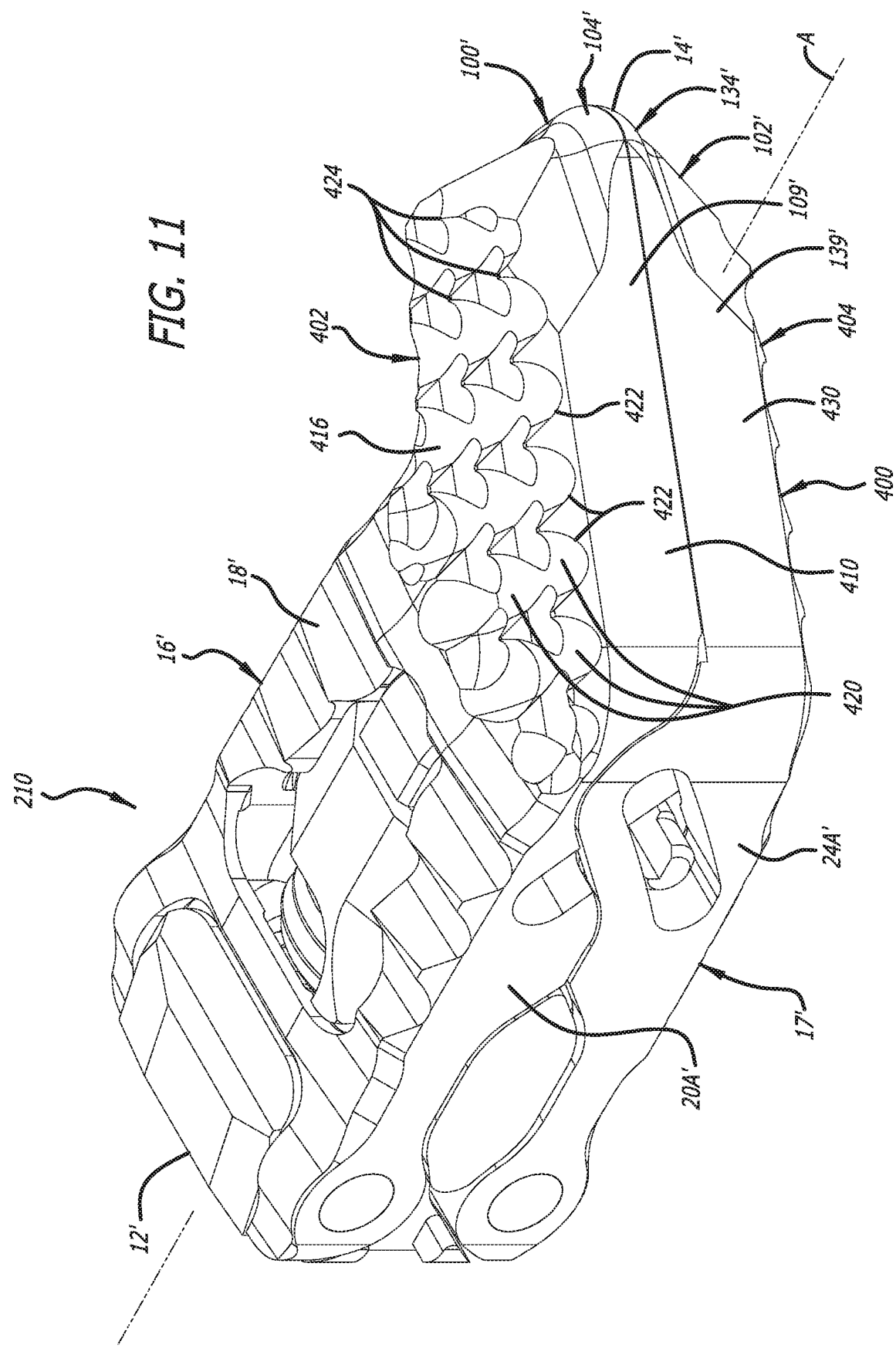
FIG. 11 is a top front perspective view of an expandable spinal implant in an unexpanded configuration.
Figure 12:
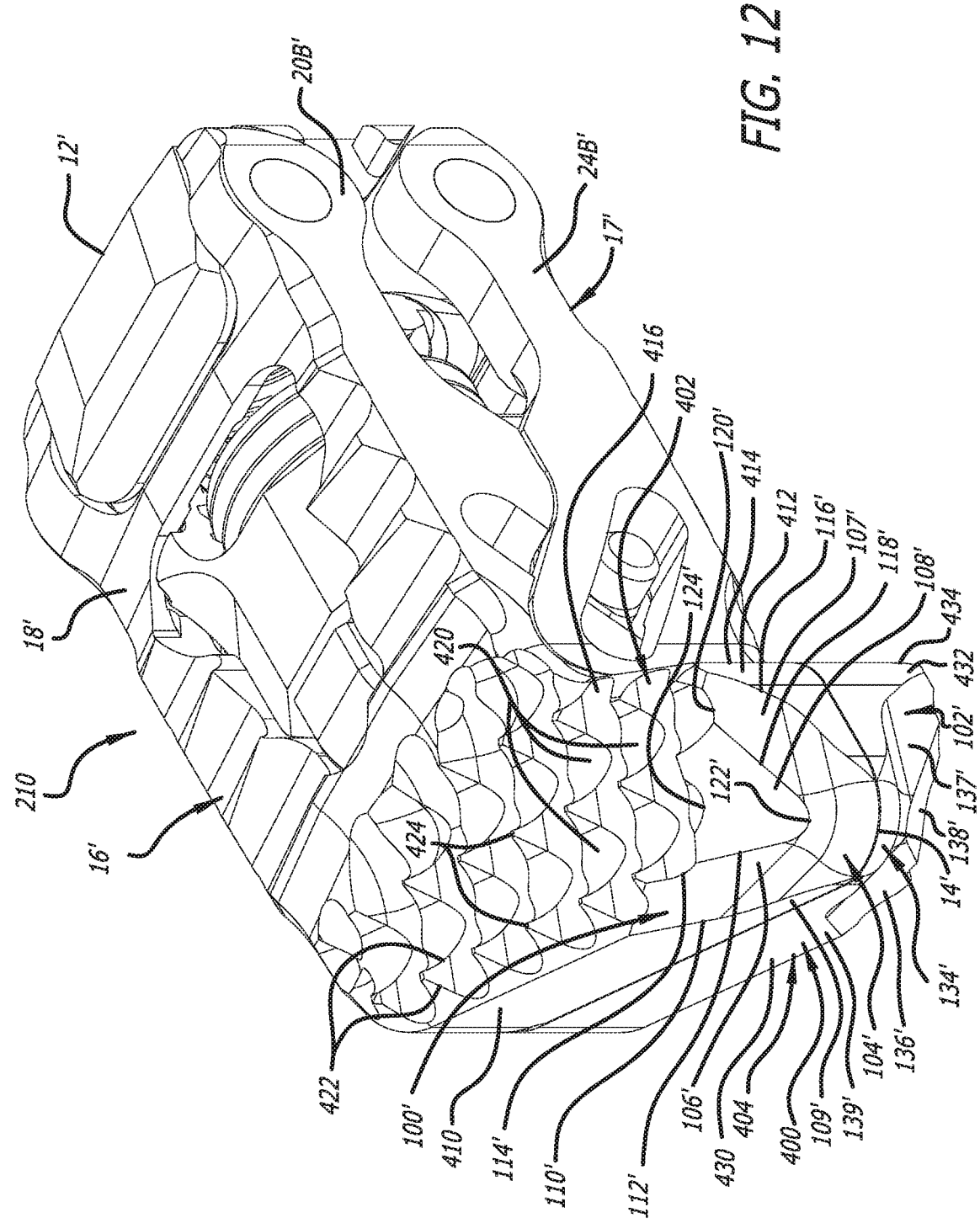
FIG. 12 is a top front perspective view of the expandable spinal implant of FIG. 11 in the unexpanded configuration.
Figure 13:
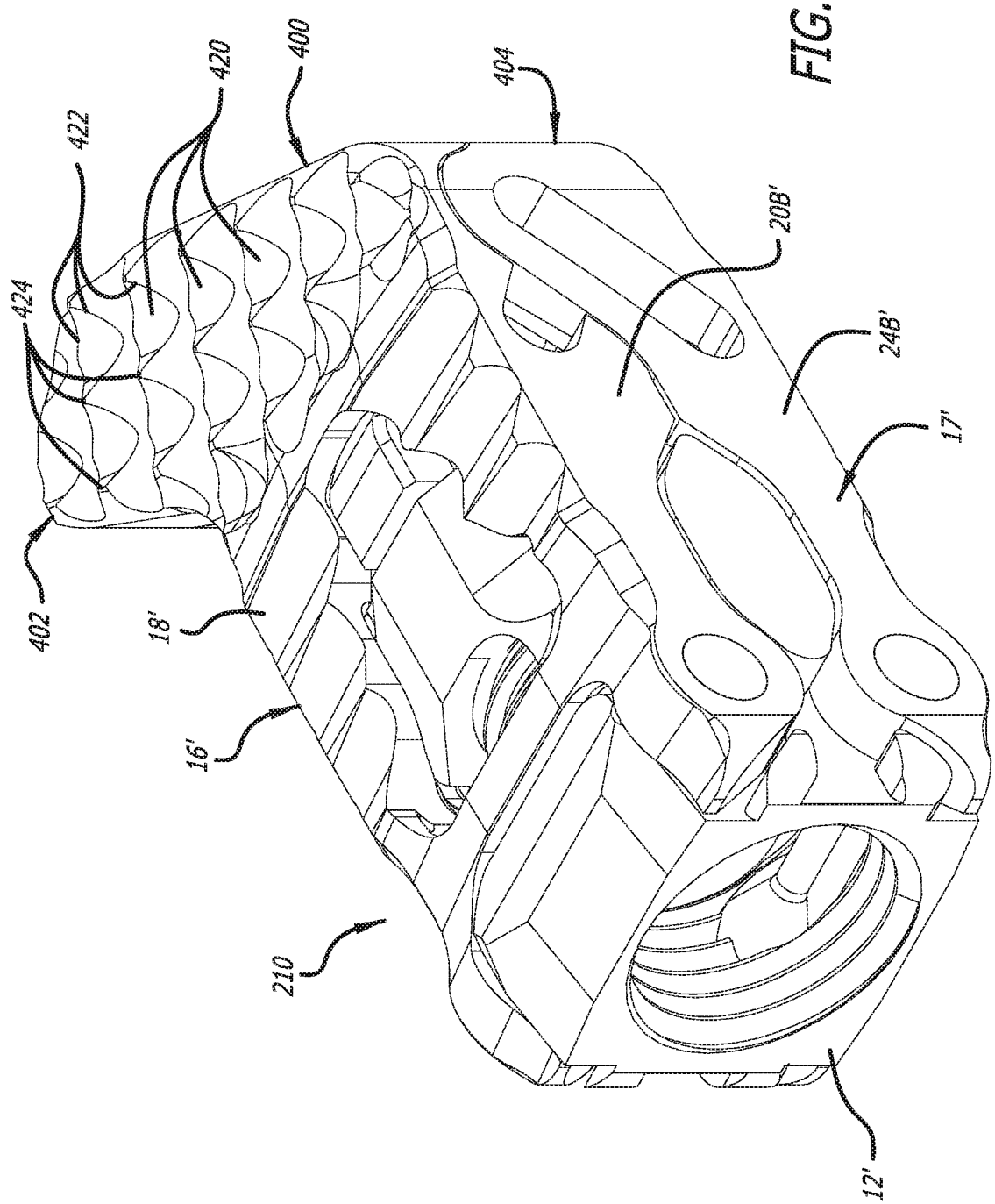
FIG. 13 is a top rear perspective view of the expandable spinal implant of FIG. 11 in the unexpanded configuration.
Figure 14:
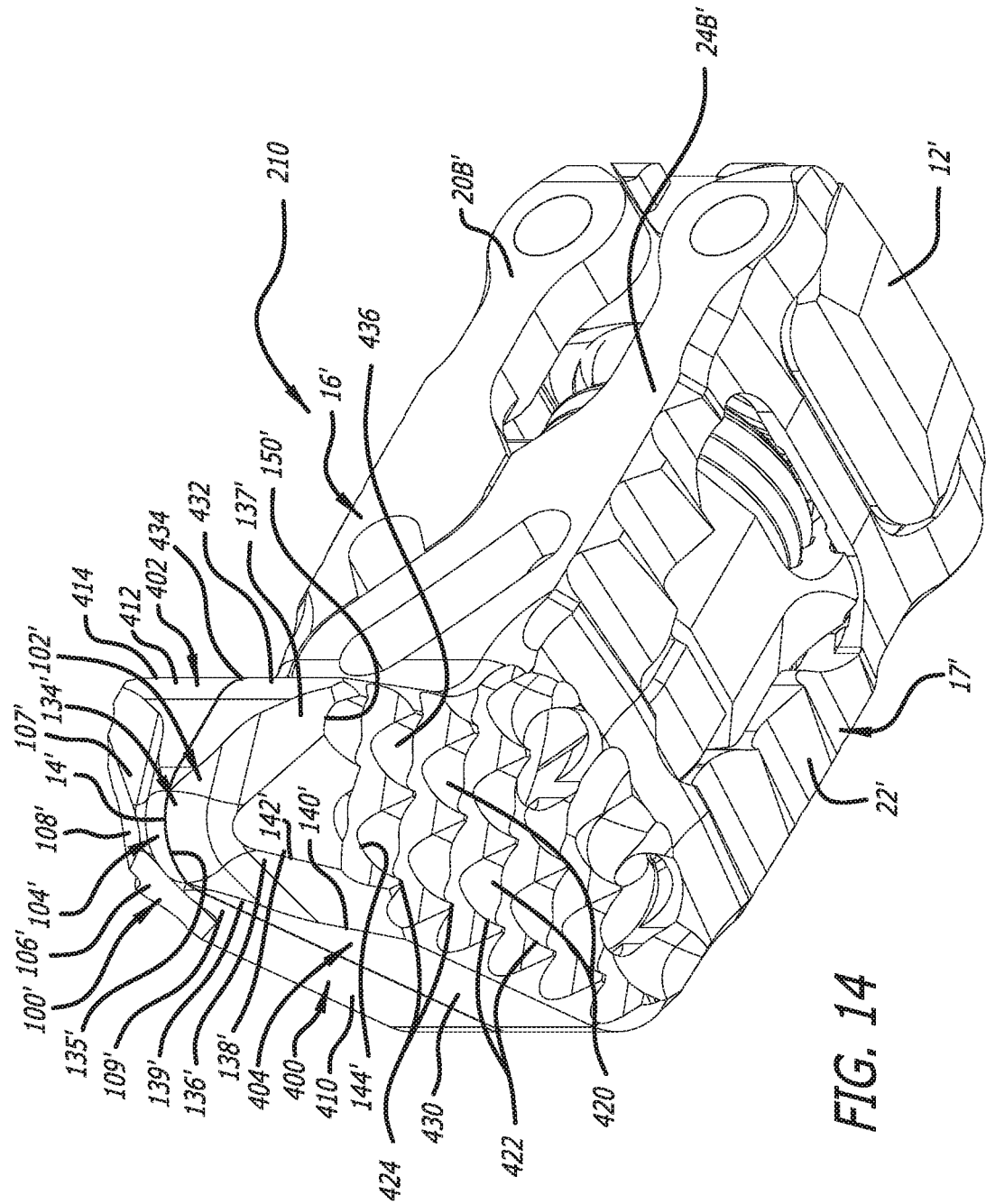
FIG. 14 is a bottom front perspective view of the expandable spinal implant of FIG. 11 in the unexpanded configuration.

As depicted in FIGS. 1-8, the spinal implant 10 has a length of 22.5 mm. The spinal implant 10 can also have larger sizes. As depicted in FIG. 9, a spinal implant 10' including the features of the spinal implant 10 has a length of 26.5 mm, and, as depicted in FIG. 10, a spinal implant 10" including the features of the spinal implant 10 has a length of 30.5 mm. Given the similarities with the spinal implant 10, the description of the spinal implant 10 is also applicable to the spinal implants 10' and 10". The various lengths of the spinal implants 10, 10', and 10" are provided to accommodate differently-sized disc spaces. Furthermore, the spinal implants 10, 10', and 10" could also include curved upper and lower surfaces similar to those depicted in FIGS. 21-24. The convexity of such curved upper and lower surface can afford additional engagement to and/or accommodation with the endplates of the first and second vertebral bodies. Furthermore, the curved upper and lower surfaces could be convex in vertical planes aligned with the mid-longitudinal axes of these spinal implants and/or convex in vertical planes perpendicular to the mid-longitudinal axes of these spinal implants. Surfaces having both convexities are called bi-convex. To essentially achieve the convexity in vertical planes perpendicular to the mid-longitudinal axis, the upper and lower surfaces of these spinal implants could be formed using a central flat cut, and lateral two side cuts at slight angles with respect to the central flat cut.

A spinal implant according to a second preferred embodiment of the present invention is generally indicated by the numeral 210 in FIGS. 11-18. As shown in FIGS. 11-18, portions of the spinal implant 210 are substantially identical to the spinal implant 10. Like the spinal implant 10, the spinal implant 210 is expandable and is configured for insertion in the disc space between the first and second vertebral bodies. Like the spinal implant 10, the spinal implant 210 can include features facilitating insertion into the disc space, can include features inhibiting withdrawal thereof from the disc space, and can include features facilitating fusion between the first and second vertebral bodies. Given the similarities between the spinal implants 10 and 210, the description of the spinal implant 10 is also applicable to the spinal implant 210, and thus, the element numbering from FIGS. 1-8 also applicable to the spinal implant 210 is not duplicated in FIGS. 11-18. Instead, like numbering is used for reference to identify various of the like elements in FIGS. 11-18. The new features of the spinal implant 210 are identified with additional element numbers.

Figure 15:
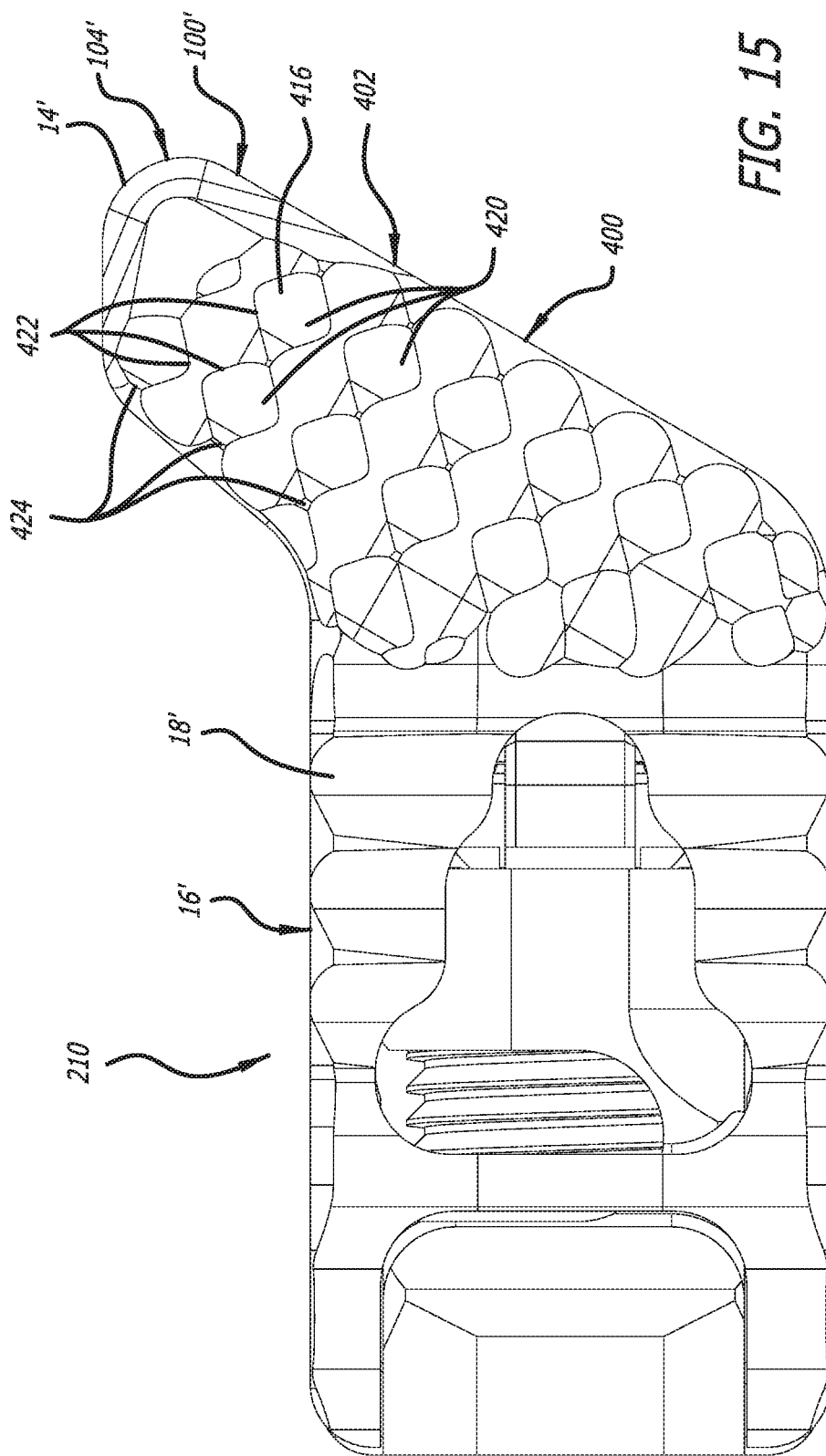
FIG. 15 is a top plan view of the expandable spinal implant of FIG. 11 in the unexpanded configuration.
Figure 16:
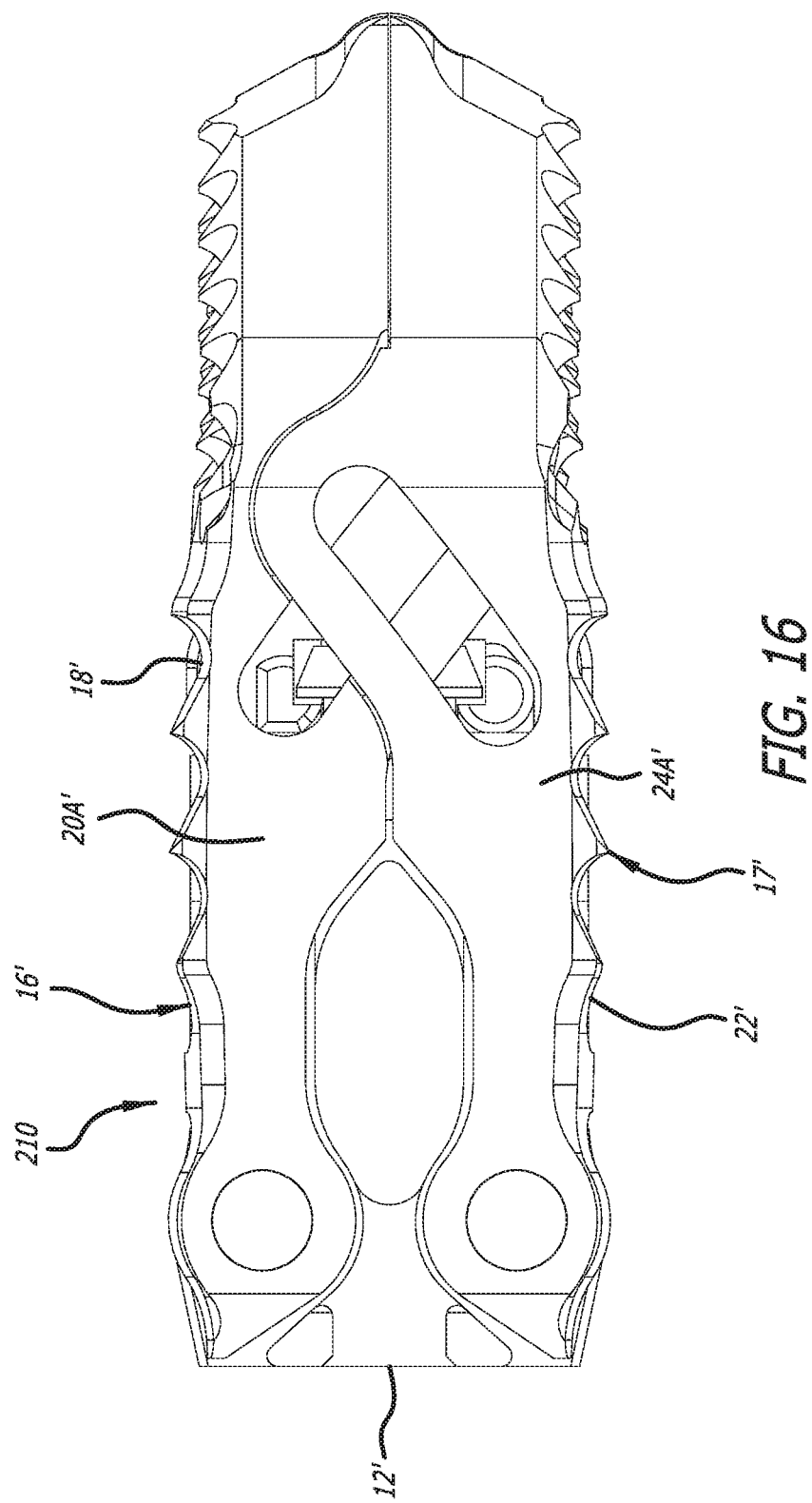
FIG. 16 is a side elevation view of the expandable spinal implant of FIG. 11 in the unexpanded configuration.
Figure 17:
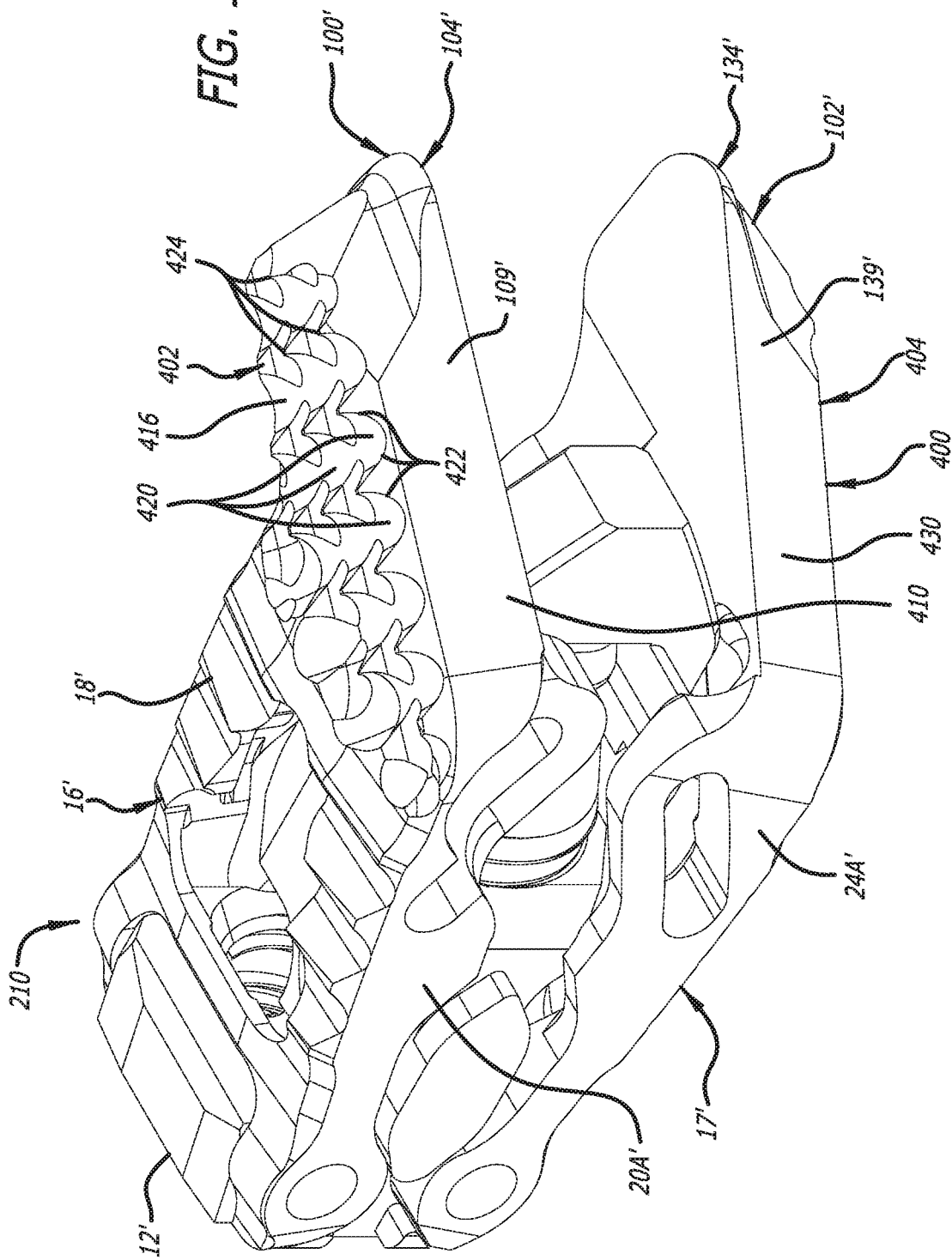
FIG. 17 is a top front perspective view of the expandable spinal implant of FIG. 11 in an expanded configuration.
Figure 18:
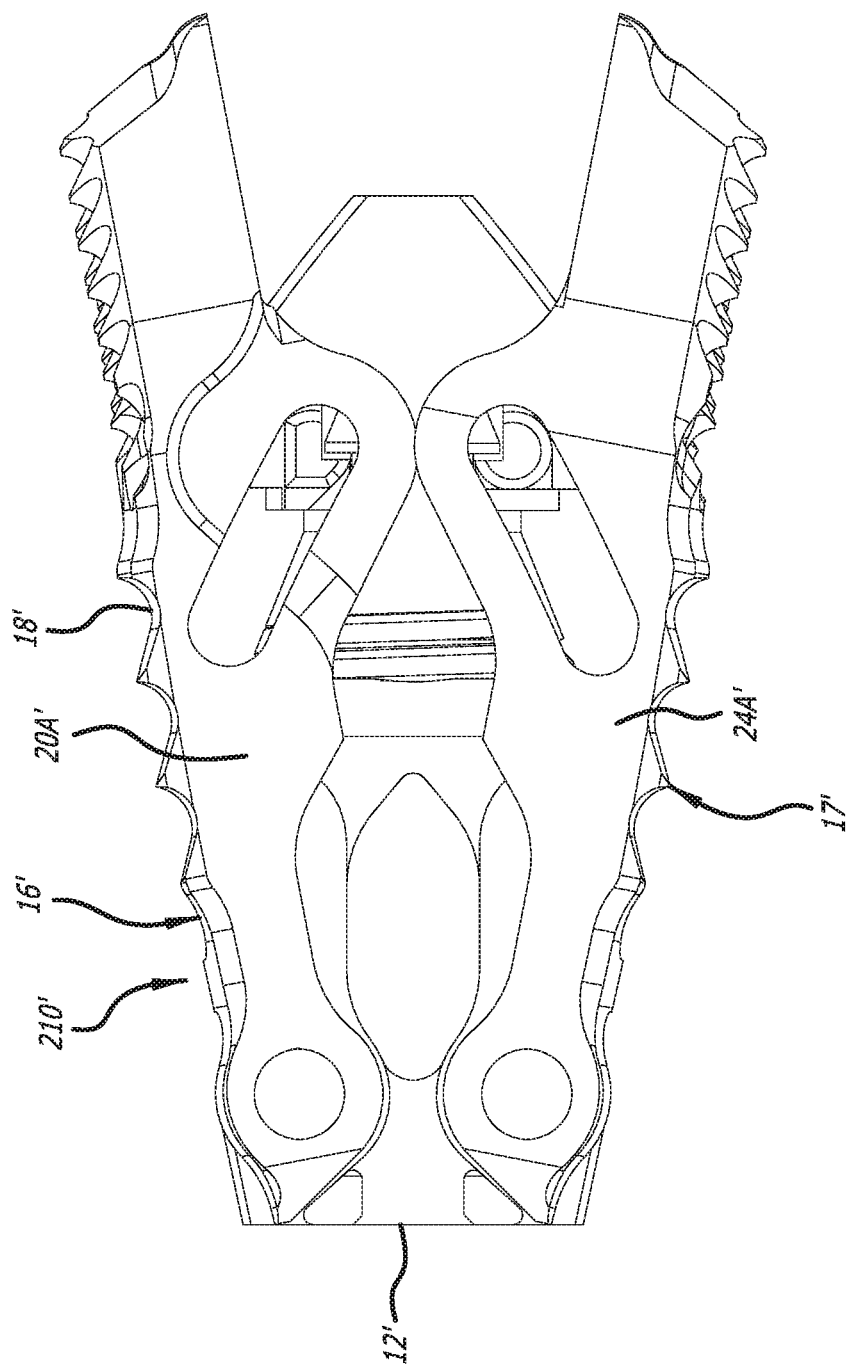
FIG. 18 is side elevational view of the expandable spinal implant of FIG. 11 in the expanded configuration.

Unlike the spinal implant 10, the spinal implant 210 is generally shaped like a hockey stick, as depicted in FIG. 15. The general hockey-stick shape of the spinal implant 210 is afforded by an extended distal end generally indicated by the numeral 400. The extended distal end 400 includes an upper portion 402 formed on the upper first end plate 16' and a lower portion 404 formed on the lower second end plate 17'. As depicted in FIGS. 11-18, the leading end portion 100' is provided on the upper portion 402 of the extended distal end portion 400, and the leading end portion 102' is provided on the lower portion 404 of the extended distal end portion 400. For example, nose portions 104' and 134' including the features of nose portions 104 and 134 are provided on the leading end 100' and the leading end 102', respectively. The description of the leading end portion 100 and the leading end portion 102 are applicable to the leading end portion 100' and the leading end portion 102'.

The upper portion 402 of the extended distal end 400 includes a front side surface 410, a lateral side surface 412, a rear-facing surface 414, and an upper surface 416. The front side surface 410 can be contiguous with the front side surface 109' of the upper first end plate 16' and can smoothly transition into the first side surface 20A'. Furthermore, the lateral side surface 412 can smoothly transition into the rear-facing surface 414, and the rear-facing surface 414 can smoothly transition into the second side surface 20B' of the upper first end plate 16'.

Furthermore, for example, the first edge 110' is formed at the intersection of the front side surface 109' with the first angled surface 106', the second edge 112' is formed at the intersection of the first angled surface 106' and the third angled surface 108', the third edge 114' is formed at the intersection of the first angled surface 106' and the upper surface 416, the fourth edge 116' is formed at the intersection of the lateral side surface 412 and the second angled surface 107', the fifth edge 118' is formed at the intersection of the second angled surface 107' with the third angled surface 108', the sixth edge 120' is formed at the intersection of the second angled surface 107' and the upper surface 416, the seventh angled surface 122' is curved, and the eighth edge 124' is formed at the intersection of the third angled surface 108' and the upper surface 416.

The upper surface 416, like the upper surface 18', can include various depressions or dimples 420 forming various ridges 422 and points 424. After placing the spinal implant 210 in the disc space, the ridges 422 and the points 424 can be used to resist movement of the spinal implant 210, and the various depressions 420 afford bone ingrowth thereinto.

The lower portion 404 of the extended distal end 400 includes a front side surface 430, a lateral side surface 432, a rear-facing surface 434, and a lower surface 436. The front side surface 430 can be contiguous with the front side surface 139' of the lower second end plate 17' and can smoothly transition into the first side surfaces 24A'. Furthermore, the lateral side surface 432 can smoothly transition into the rear-facing surface 434, and the rear-facing surface 434 can smoothly transition into the second side surface 24B' of the lower second end plate 17'.

Furthermore, for example, the first edge 140' is partially formed at the intersection of the front side surface 139' with the first angled surface 136', the second edge 142' is formed at the intersection of the first angled surface 136' and the third angled surface 138', the third edge 144' is formed at the intersection of the first angled surface 136' and the lower surface 436, the fourth edge 146' is partially formed at the intersection of the lateral side surface 432 and the second angled surface 137', the fifth edge 148' is formed at the intersection of the second angled surface 137' with the third angled surface 108', the sixth edge 150' is formed at the intersection of the second angled surface 137' and the lower surface 436, the seventh edge 152' is curved, and the eighth edge 154' is formed at the intersection of the third angled surface 138' and the lower surface 436.

The lower surface 436, like the lower surface 22', can include various depressions or dimples 440 forming various ridges 442 and points 444. After placing the spinal implant 210 in the disc space, the ridges 442 and the points 444 can be used to resist movement of the spinal implant 210, and the various depressions 440 afford bone growth thereinto.

Figure 19:
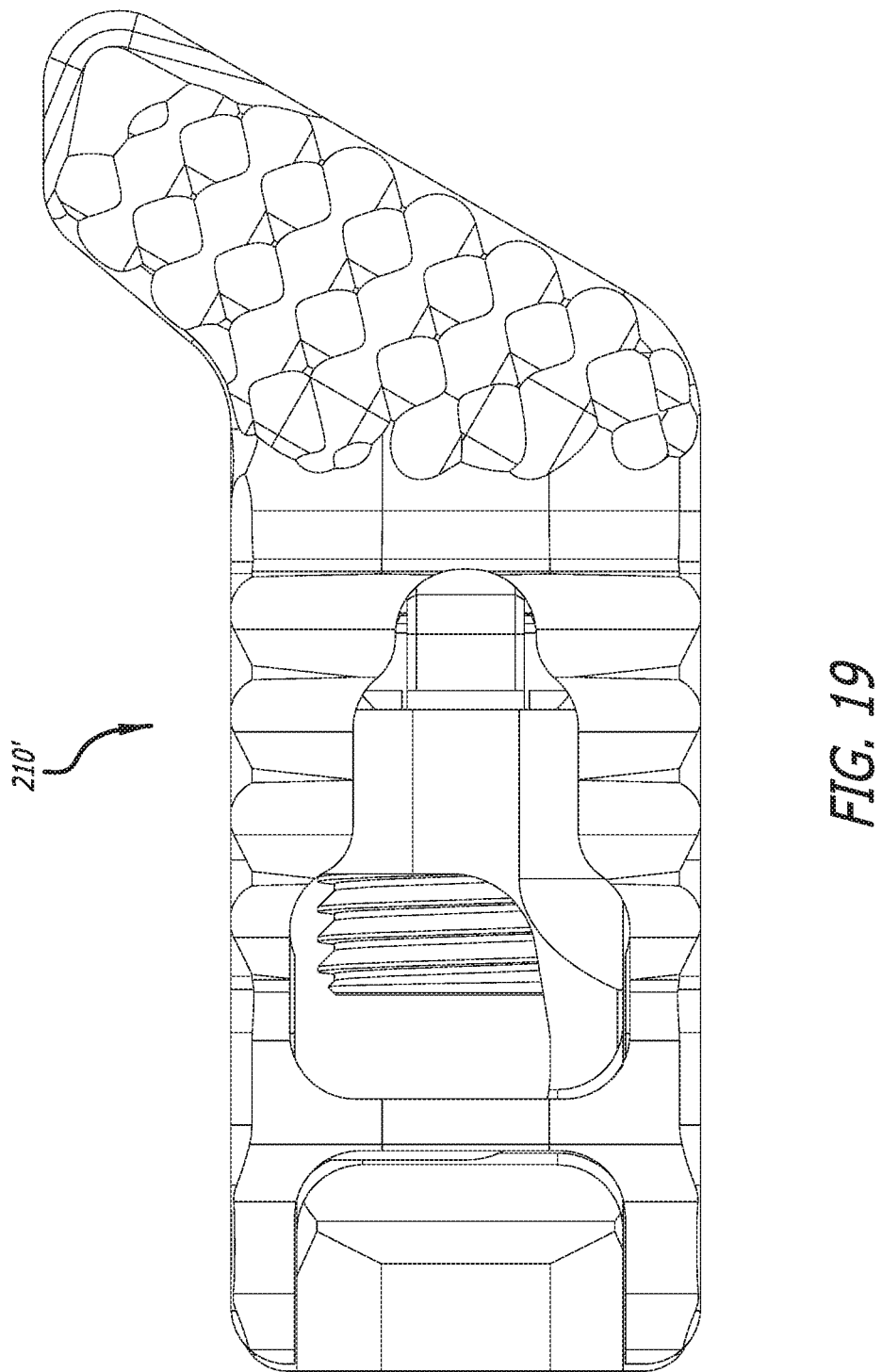
FIG. 19 is a top plan view of an expandable spinal implant similar to that of FIG. 11 in an expanded configuration and having a first larger size.
Figure 20:
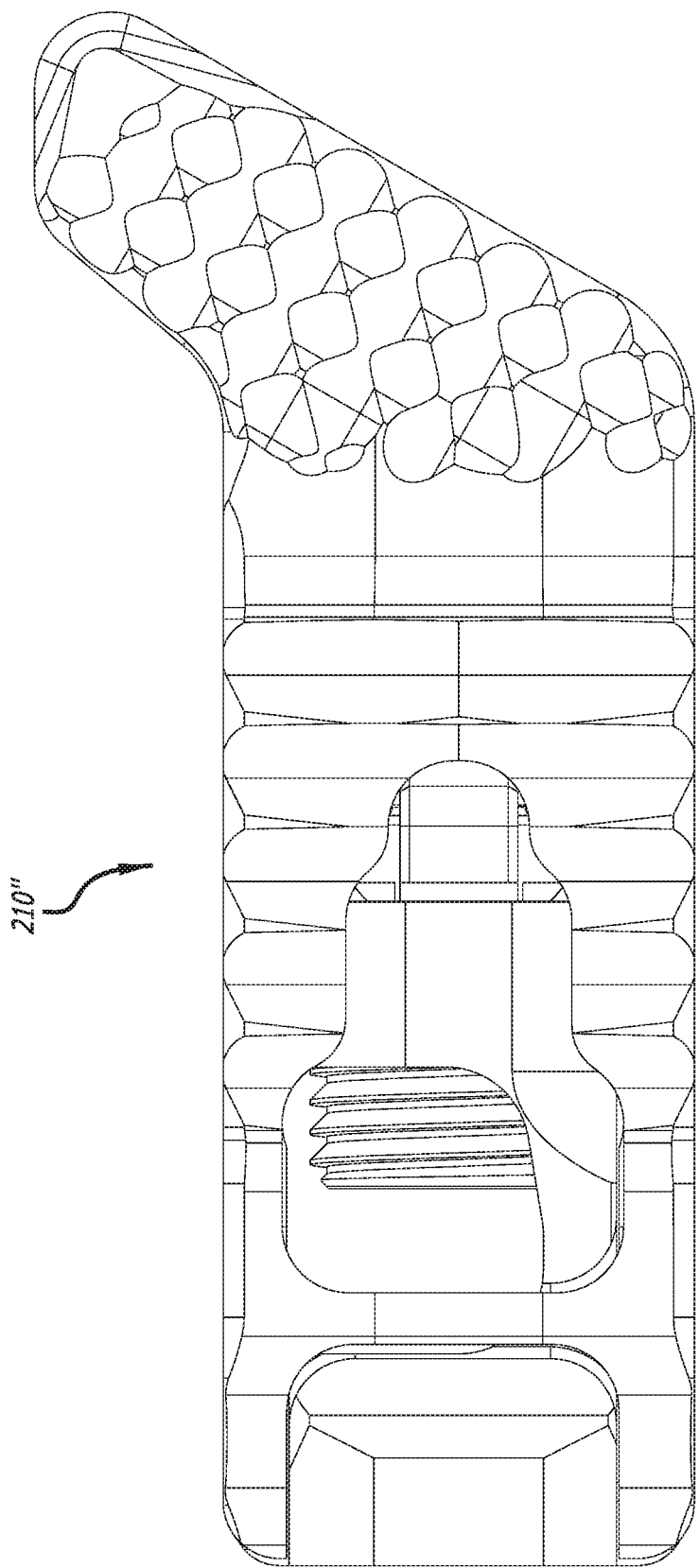
FIG. 20 is a top plan view of an expandable spinal implant similar to that of FIG. 11 in an expanded configuration and having a second larger size.
Figure 21:
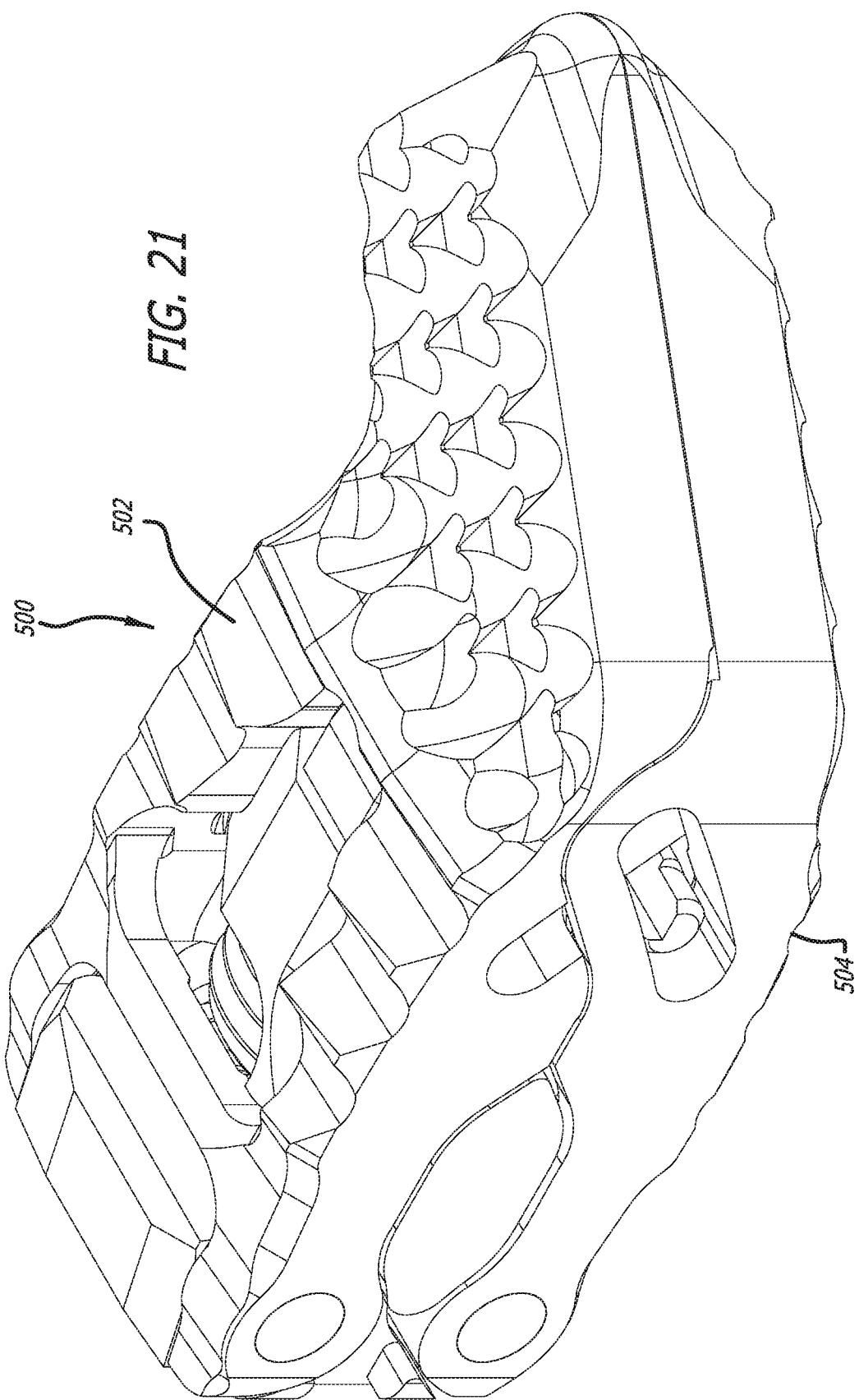
FIG. 21 is a top side perspective view of an expandable spinal implant similar to that of FIG. 11 in an unexpanded configuration and having convex upper and lower surfaces of a first curvature.
Figure 22:
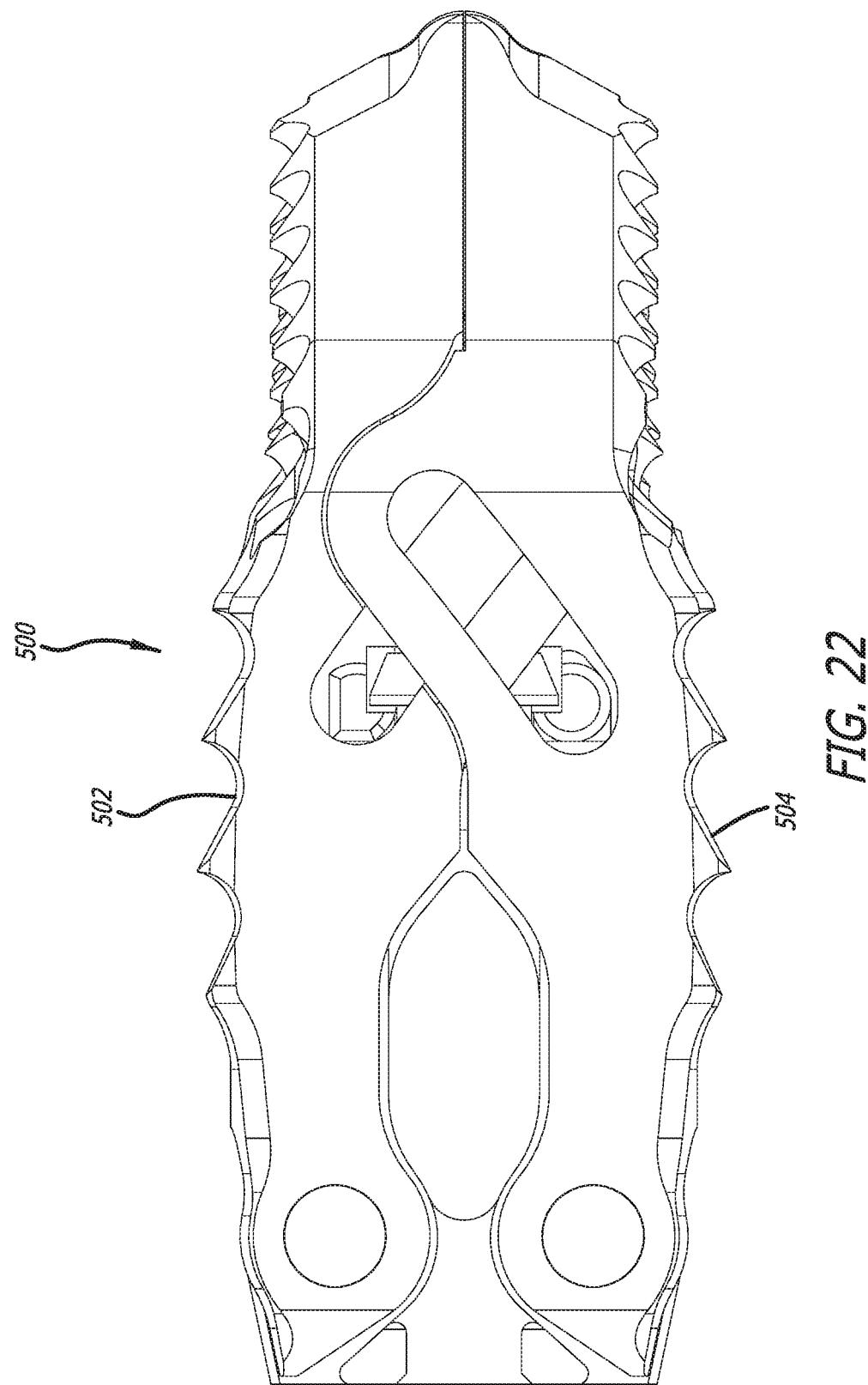
FIG. 22 is a side elevational view of the expandable implant of FIG. 21 in the unexpanded configuration.
Figure 23:
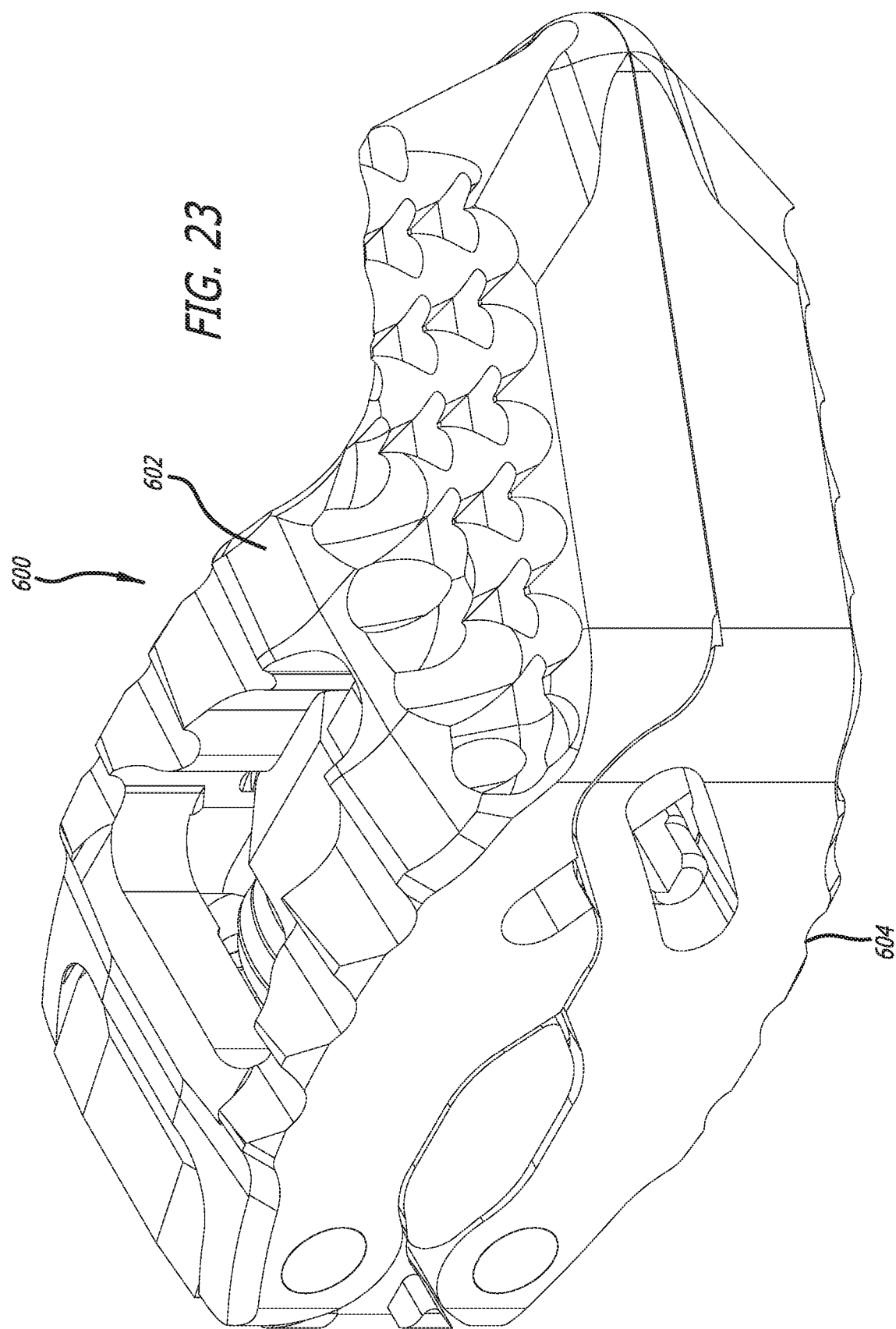
FIG. 23 is a top side perspective view of an expandable spinal implant similar to that of FIG. 11 in an unexpanded configuration and having convex upper and lower surfaces of a second curvature.
Figure 24:
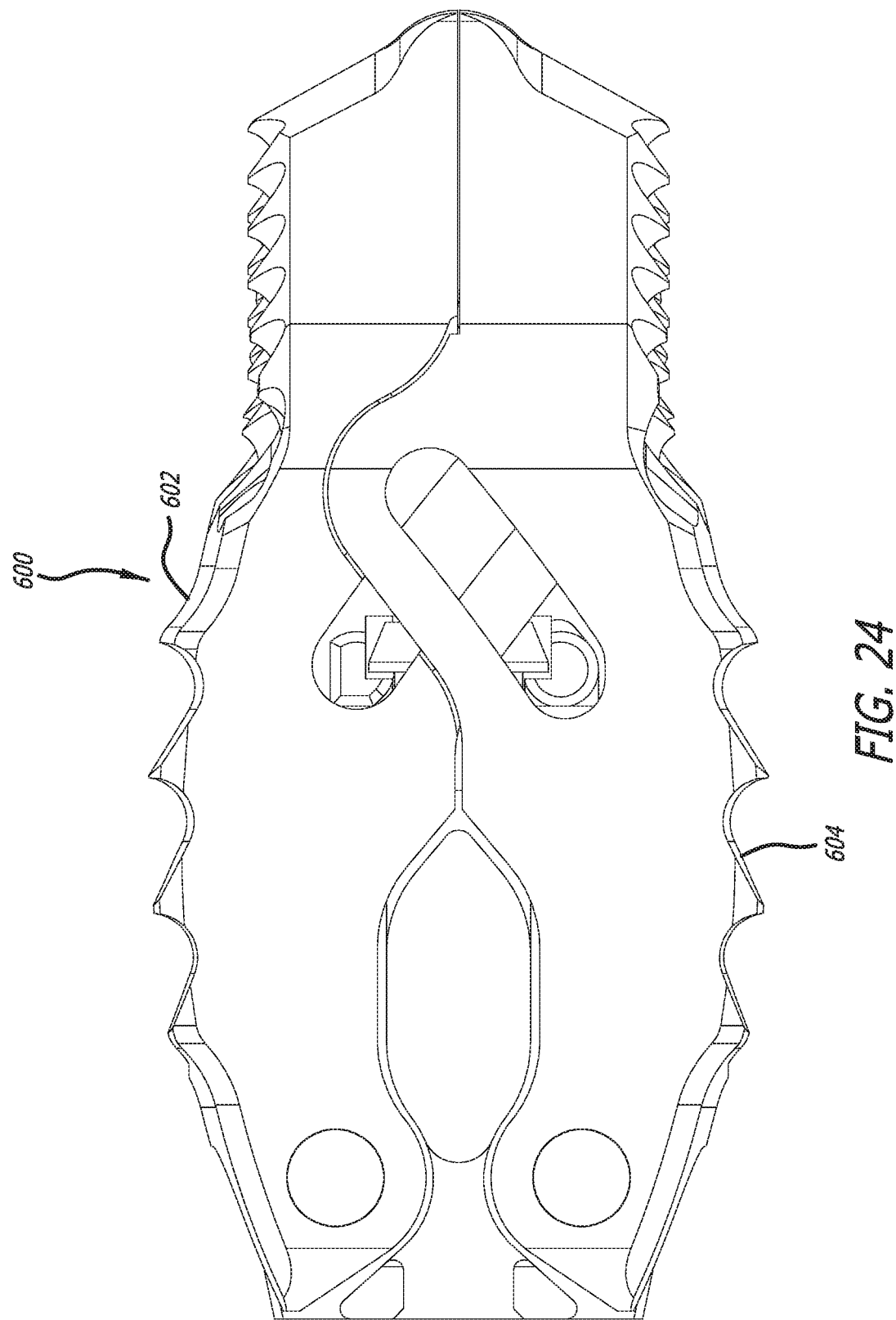
FIG. 24 is a side elevational view of the expandable implant of FIG. 23 in the unexpanded configuration.

As depicted in FIGS. 11-18, the spinal implant 210 has a length of 25.0 mm. The spinal implant 210 can also have larger sizes. As depicted in FIG. 19, a spinal implant 210' including the features of the spinal implant 210 has a length of 29.0 mm, and, as depicted in FIG. 20, a spinal implant 210" including the features of the spinal implant 210 has a length of 33 mm. Given the similarities with the spinal implant 210, as well as the spinal implant 10, the descriptions of the spinal implant 10 and the spinal implant 210 are applicable to the spinal implants 210' and 210". The various lengths of the spinal implant 210, the spinal implant 210', and the spinal implant 210" are provided to accommodate differently-sized disc spaces.

As depicted in FIGS. 21-24, additional embodiments of the spinal implant 210 can include upper and lower surfaces that can have varying degrees of convexity. To illustrate, a spinal implant 500 depicted in FIGS. 21 and 22 and a spinal implant 600 depicted in FIGS. 23 and 24 have different degrees of convexity on their upper and lower surfaces. The spinal implants 500 and 600 share many of their features with the spinal implant 10 and the spinal implant 210. Given the similarities with the spinal implant 10 and the spinal implant 210, the descriptions of the spinal implant 10 and the spinal implant 210 are applicable to the spinal implants 500 and 600. Thus, the element numbering applicable to the spinal implant 10 and the spinal implant 210 is also applicable to the spinal implants 500 and 600 and is not duplicated in FIGS. 21-24.

The spinal implant 500 includes a curved upper surface 502 and a curved lower surface 504, and the spinal implant 600 includes a curved upper surface 602 and a curved lower surface 604. The convexities of the curved upper surface 502 and the curved lower surface 504, and the convexities of the curved upper surface 602 and the curved lower surface 604 occur in planes aligned with the mid-longitudinal axes of these implants. The curved upper and lower surfaces 502 and 504 can have a root radius of curvature ranging from R10 mm to R1000 mm, and the curved upper and lower surfaces 602 and 604 can have a root radius of curvature ranging from R10 mm to R1000 mm. Furthermore, the curved upper and lower surfaces also could be convex in vertical planes perpendicular to the mid-longitudinal axes of these spinal implants. Surfaces having both convexities are called bi-convex. To essentially achieve the convexity in vertical planes perpendicular to the mid-longitudinal axis, the upper and lower surfaces of these spinal implants could be formed using a central flat cut, and lateral two side cuts at slight angles with respect to the central flat cut. Because the endplates of the first and second vertebral bodies have varying degrees of concavities, the convexities of the spinal implants 500 and 600 can afford additional engagement with the endplates.

In addition to the expandable spinal implants discussed above, features at the leading ends thereof configured to facilitate ease of insertion into the disc space can also be incorporated into non-expandable implants and implant trails. Furthermore, non-expandable implants can also incorporate the features of the upper and lower surface (including the above-described depressions or dimples). These features can be incorporated on non-expandable implants and implant trials with and without having a hockey-stick shape.

Figure 25:
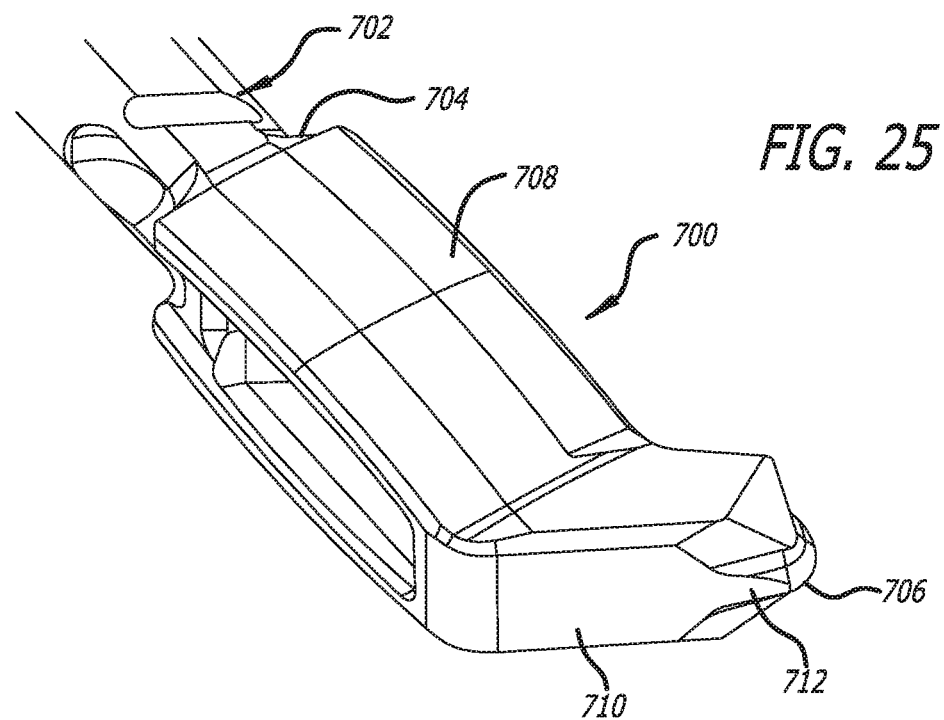
FIG. 25 is a top perspective view of an implant trial incorporating features of the expandable implant of FIG. 11.
Figure 26:
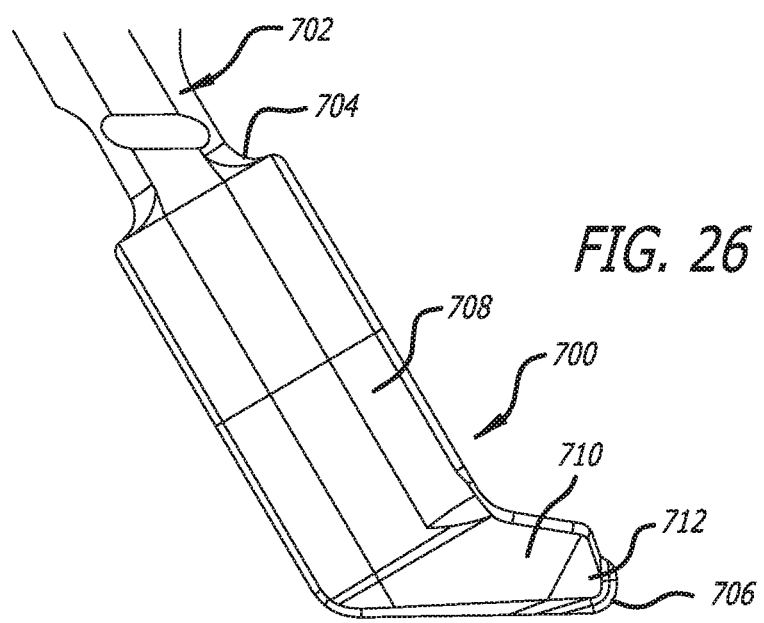
FIG. 26 is a top plan view of the implant trial of FIG. 25.

FIGS. 25 and 26 illustrate an implant trial 700 including the features of the above-discussed expandable spinal implants. The implant trial 700 has a hockey-stick shape and is inserted into the disc space using an insertion instrument 702. The implant trial 700 includes a proximal end 704, an opposite distal end 706, a body portion 708, an extended distal end 710, and a leading end portion 712. The leading end portion 712 includes the features of the leading end portions 100' and 102' of the expandable spinal implant 210 and the descriptions thereof are directly applicable to the leading end portion 712.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A spinal implant comprising:
a proximal end, an opposite distal end, a length between the proximal end and the distal end, and a mid-longitudinal axis extending along the length through the proximal end and the distal end,
a frame portion provided at and adjacent the proximal end, the frame portion including a first end portion, a second end portion, and a threaded aperture formed therethrough, the first end portion being closer to the proximal end than the second end portion, and the threaded aperture extending between the first end portion and the second end portion;
a threaded plug and a head portion operatively connected to the threaded plug, the threaded plug being received in the threaded aperture, the head portion being moveable from a first position closer to the proximal end to a second position closer to the distal end via rotation of the threaded plug in the threaded aperture, and the head portion including an upper first ramp and a lower second ramp;
an upper first end plate portion being configured to engage at least a portion of an end plate of the upper vertebral body when the spinal implant is inserted into a disc space between upper and lower vertebral bodies, the upper first end plate portion including a first ramp portion engageable to the upper first ramp of the head portion,
a lower second end plate portion being configured to engage at least a portion of an end plate of the lower vertebral body when the spinal implant is inserted into the disc space between the upper and lower vertebral bodies, the lower second end plate portion including a second ramp portion engageable to the lower second ramp of the head portion, and
the upper first end plate portion including a first leading end portion having a first nose portion and a first angled surface, the first nose portion being configured to facilitate initial insertion of the spinal implant into the disc space,
the lower second end plate portion including a second leading end portion having a second nose portion and a second angled surface, the second nose portion being configured to facilitate initial insertion of the spinal implant into the disc space, and
the upper first end plate portion and the lower second end plate portion each being pivotally attached to the frame portion, and being pivotally moveable with respect to one another to facilitate movement of the spinal implant between an unexpanded configuration and an expanded configuration;
wherein movement of the head portion from the first position toward the second positon forces the first ramp to move along the first portion to pivot the upper first end plate portion, and forces the second ramp to move along the second ramp portion to pivot the lower second end plate portion, the pivoting of the upper first end plate portion and the lower second end plate portion moving the spinal implant from the unexpanded configuration to the expanded configuration;
wherein a first plane bisecting the spinal implant into an upper portion and a lower portion extends through the proximal end, the distal end, and along the mid-longitudinal axis,
wherein a second plane perpendicular to the first plane and transverse to the mid-longitudinal axis bisects each of the first nose portion and the second nose portion, the first nose portion and the second nose portion being at least in part arcuate in the second plane, and
wherein the first leading end portion and the second leading end portion each extend from a third plane perpendicular to the second plane to the distal end, the first angled surface tapering toward the first nose portion in the second plane, and the second angled surface tapering toward the second nose portion in the second plane.

2. The spinal implant of claim 1, further comprising a third angled surface and a fourth angled surface on the first leading end portion extending from the first nose portion to the upper surface, the third angled surface being provided on one side of the first angled surface and the fourth angled surface being provided on the other side of the first angled surface, wherein the third angled surface and the fourth angled surface both smoothly transition into the first nose portion.

3. The spinal implant of claim 2, further comprising a fifth angled surface and a sixth angled surface on the second leading end portion extending from the second nose portion to the lower surface, the fifth angled surface being provided on one side of the second angled surface and the sixth angled surface being provided on the other side of the second angled surface, wherein the fifth angled surface and the sixth angled surface both smoothly transition into the second nose portion.

4. The spinal implant of claim 1, wherein distances between the first plane and the first angled surface of the first leading end portion in the second plane decrease from the third plane to the distal end, and distances between the first plane and the second angled surface of the second leading end portion in the second plane decrease from the third plane to the distal end.

5. The spinal implant of claim 1, wherein the first nose portion and the second nose portion extend between a fourth plane and a fifth plane, the fourth plane and the fifth plane being parallel to the mid-longitudinal axis and the first plane, the distance between the fourth plane and the fifth plane at the intersection with the second plane being less than a third of a distance between the upper surface and the lower surface in the second plane.

6. The spinal implant of claim 5, wherein distances between the first plane and the first angled surface of the first leading end portion in the second plane decrease from the third plane to the distal end, and distances between the first plane and the second angled surface of the second leading end portion in the second plane decrease from the third plane to the distal end.

7. The spinal implant of claim 1, wherein:
a fourth plane parallel to the third plane intersects the first leading end portion and the second leading end portion halfway between the third plane and the distal end,
a fifth plane parallel to the third plane intersects the first leading end portion and the second leading end portion halfway between the third plane and the fourth plane,
a sixth plane parallel to the third plane intersects the first leading end portion and the second leading end portion halfway between the fourth plane and the distal end,
a distance between the first angled surface and the second angled surface in the second plane at the intersection of the fourth plane being greater than a distance between the first angled surface and the second angled surface in the second plane at the intersection of the sixth plane, and
a distance between the first angled surface and the second angled surface in the second plane at the intersection of the fifth plane being greater than a distance between the first angled surface and the second angled surface in the second plane at the intersection of the fourth plane.

8. The spinal implant of claim 1, wherein one of the upper surface of the upper first end plate portion and the lower surface of the lower second end plate portion includes at least two depressions formed thereon, the intersection of the at least two depressions forming a ridge.

9. The spinal implant of claim 8, wherein the other of the upper surface of the upper first end plate portion and the lower surface of the lower second end plate portion includes at least two depressions formed thereon, the intersection of the at least two depressions forming a ridge.

10. The spinal implant of claim 1, wherein the upper first end plate portion includes a first lateral portion and a first slot with a first orientation formed in the in the first lateral portion, the lower second end plate portion includes a second lateral portion and a second slot with a second orientation formed in the second lateral portion, and the head portion includes a first post and a second post, the first post being received in the first slot and the second post being received in the second slot, the first orientation and the interaction of the first post in the first slot forcing the upper first end plate portion to pivot as the head portion moves from the first position toward the second position, and the second orientation and the interaction of the second post in the second slot forcing the lower second end plate portion to pivot as the head portion moves from the first position toward the second position.

11. A spinal implant comprising:
a proximal end, an opposite distal end, a length between the proximal end and the distal end, and a mid-longitudinal axis extending along the length through the proximal end and the distal end,
an upper first end plate portion including an upper surface being configured to engage at least a portion of an end plate of the upper vertebral body when the spinal implant is inserted into a disc space between upper and lower vertebral bodies,
a lower second end plate portion including a lower surface being configured to engage at least a portion of an end plate of the lower vertebral body when the spinal implant is inserted into the disc space between the upper and lower vertebral bodies, and
a frame portion provided at and adjacent the proximal end the frame portion including a first end portion, a second end portion, and a threaded aperture formed therethrough the first end portion being closer to the proximal end than the second end portion, and the threaded aperture extending between the first end portion and the second end portion;
a threaded plug and a head portion operatively connected to the threaded plug, the threaded plug being received in the threaded aperture, the head portion being moveable from a first position closer to the proximal end to a second position closer to the distal end via rotation of the threaded plug in the threaded aperture, and the head portion including an upper first ramp and a lower second ramp:
the upper first end plate portion including a first leading end portion including a first nose portion and at least a first angled surface extending from the first nose portion to the upper surface, the upper first end plate portion including a first ramp portion engageable to the upper first ramp of the head portion,
the lower second end plate portion including a second leading end portion including a second nose portion and at least a second angled surface extending from the second nose portion to the lower surface, the lower second end plate portion including a second ramp portion engageable to the lower second ramp of the head portion, and
the upper first end plate portion and the lower second end plate portion each being pivotally attached to the frame portion, and being pivotally moveable with respect to one another to facilitate movement of the spinal implant between an unexpanded configuration and an expanded configuration;
wherein movement of the head portion from the first position toward the second position forces the first ramp to move along the first ramp portion to pivot the upper first end plate portion and forces the second ramp to move along the second ramp portion to pivot the lower second end plate portion, the pivoting of the upper first end plate portion and the lower second end plate portion moving the spinal implant from the unexpanded configuration to the expanded configuration:
wherein a first plane bisecting the spinal implant into an upper portion and a lower portion extends through the proximal end and the distal end, wherein a second plane perpendicular to the first plane and transverse to the mid-longitudinal axis bisects each of the first nose portion and the second nose portion, the first nose portion and the second nose portion being at least in part arcuate in the second plane, and wherein the first leading end portion and the second leading end portion each extend from a third plane perpendicular to the second plane to the distal end.

12. The spinal implant of claim 11, wherein the first nose portion and the second nose portion extend between a fourth plane and a fifth plane, the fourth plane and the fifth plane being parallel to the mid-longitudinal axis and the first plane, the distance between the fourth plane and the fifth plane at the intersection with the second plane being less than a third of a distance between the upper surface and the lower surface in the second plane.

13. The spinal implant of claim 11, wherein distances between the first plane and the first angled surface of the first leading end portion in the second plane decrease from the third plane to the distal end, and distances between the first plane and the second angled surface of the second leading end portion in the second plane decrease from the third plane to the distal end.

14. The spinal implant of claim 11, wherein:
a fourth plane parallel to the third plane intersects the first leading end portion and the second leading end portion halfway between the third plane and the distal end,
a fifth plane parallel to the third plane intersects the first leading end portion and the second leading end portion halfway between the third plane and the fourth plane,
a sixth plane parallel to the third plane intersects the first leading end portion and the second leading end portion halfway between the fourth plane and the distal end,
a distance between the first angled surface and the second angled surface in the second plane at the intersection of the fourth plane being greater than a distance between the first angled surface and the second angled surface in the second plane at the intersection of the sixth plane, and
a distance between the first angled surface and the second angled surface in the second plane at the intersection of the fifth plane being greater than a distance between the first angled surface and the second angled surface in the second plane at the intersection of the fourth plane.

15. The spinal implant of claim 11, wherein one of the upper surface of the upper first end plate portion and the lower surface of the lower second end plate portion includes at least two depressions formed thereon, the intersection of the at least two depressions forming a ridge.

16. The spinal implant of claim 15, wherein the other of the upper surface of the upper first end plate portion and the lower surface of the lower second end plate portion includes at least two depressions formed thereon, the intersection of the at least two depressions forming a ridge.

17. The spinal implant of claim 11, wherein the upper first end plate portion includes a first lateral portion and a first slot with a first orientation formed in the in the first lateral portion, the lower second end plate portion includes a second lateral portion and a second slot with a second orientation formed in the second lateral portion, and the head portion includes a first post and a second post, the first post being received in the first slot and the second post being received in the second slot, the first orientation and the interaction of the first post in the first slot forcing the upper first end plate portion to pivot as the head portion moves from the first position toward the second position, and the second orientation and the interaction of the second post in the second slot forcing the lower second end plate portion to pivot as the head portion moves from the first position toward the second position.

18. A spinal implant comprising:
a proximal end, an opposite distal end, and a mid-longitudinal axis extending through the proximal end and the distal end,
a frame portion provided at and adjacent the proximal end, the frame portion including a first end portion, a second end portion, and a threaded aperture formed therethrough, the first end portion being closer to the proximal end than the second end portion, and the threaded aperture extending between the first end portion and the second end portion;
a threaded plug and a head portion operatively connected the threaded plug the threaded plug being received in the threaded aperture, the head portion being moveable from a first position closer to the proximal end to a second position closer to the distal end via rotation of the threaded plug in the threaded aperture and the head portion including an upper first ramp and a lower second ramp;
an upper first end plate portion including an upper surface configured to engage at least a portion of an end plate of the upper vertebral body when the spinal implant is inserted into a disc space between upper and lower vertebral bodies, the upper first end plate portion including a first ramp portion engageable to the upper first ramp of the head portion,
a lower second end plate portion including a lower surface configured to engage at least a portion of an end plate of the lower vertebral body when the spinal implant is inserted into the disc space between the upper and lower vertebral bodies, the lower second end plate portion including a second ramp portion engageable to the lower second ramp of the head portion, and
the upper first end plate portion including a first lateral portion with a first lateral surface on a first side of the spinal implant,
the lower second end plate portion including a second lateral portion with a second lateral surface on the first side of the spinal implant,
an upper first extension portion formed contiguously with the upper first end plate, the upper first extension portion having a first leading end including a first nose portion and a first angled surface, at least the first nose portion being positioned on an opposite side of a first plane extending along at least one of the first lateral surface and the second lateral surface than a second plane parallel to the first plane and extending through the mid-longitudinal axis,
a lower second extension portion formed contiguously with the lower second end plate, the lower second extension portion having a second leading end including a second nose portion and a second angled surface, at least the second nose portion being positioned on an opposite side of the first plane than the second plane, and
the upper first end plate portion and the lower second end plate portion each being pivotally attached to the frame portion, and being pivotally moveable with respect to one another to facilitate movement of the spinal implant between an unexpanded configuration and an expanded configuration;
wherein movement of the head portion from the first position toward the second position forces the first ramp to move along the first ramp portion to pivot the upper first end plate portion, and forces the second ramp to move along the second ramp portion to pivot the lower second end plate portion the pivoting of the upper first end plate portion and lower second end plate portion moving the spinal implant from the unexpanded configuration to the ended configuration:

wherein a third plane bisecting the spinal implant into an upper portion and a lower portion extends through the proximal end, the distal end, and along the mid-longitudinal axis, wherein a fourth plane perpendicular to the third plane and transverse to the mid-longitudinal axis bisects each of the first nose portion and the second nose portion, the first nose portion and the second nose portion being at least in part arcuate in the fourth plane, and wherein the first leading end portion and the second leading end portion each extend from a fifth plane perpendicular to the fourth plane to the distal end, the first angled surface of the first leading end portion tapering toward the first nose portion in the fourth plane, and the second angled surface of the second leading end portion tapering toward the second nose portion in the fourth plane.

19. The spinal implant of claim 18, wherein distances between the third plane and the first angled surface of the first leading end portion in the fourth plane decrease from the fifth plane to the distal end, and distances between the third plane and the second angled surface of the second leading end portion in the fourth plane decrease from the fifth plane to the distal end.

20. The spinal implant of claim 18, wherein the first nose portion and the second nose portion extend between a sixth plane and a seventh plane, the sixth plane and the seventh plane being parallel to the mid-longitudinal axis and the third plane, the distance between the sixth plane and the seventh plane at the intersection with the fourth plane being less than a third of a distance between the upper surface and the lower surface in the fourth plane.

21. The spinal implant of claim 18, wherein:

a sixth plane parallel to the fifth plane intersects the first leading end portion and the second leading end portion halfway between the fifth plane and the distal end, a seventh plane parallel to the fifth plane intersects the first leading end portion and the second leading end portion halfway between the fifth plane and the sixth plane, an eighth plane parallel to the fifth plane intersects the first leading end portion and the second leading end portion halfway between the sixth plane and the distal end, a distance between the first angled surface and the second angled surface in the fourth plane at the intersection of the sixth plane being greater than a distance between the first angled surface and the second angled surface in the fourth plane at the intersection of the eighth plane, and a distance between the first angled surface and the second angled surface in the fourth plane at the intersection of the seventh plane being greater than a distance between the first angled surface and the second angled surface in the fourth plane at the intersection of the sixth plane.

22. The spinal implant of claim 18, wherein the upper first extension portion includes an upper surface and the lower second extension portion includes a lower surface, each of the upper surface of the upper first extension portion and the lower surface of the lower second extension portion including at least two depressions formed thereon, the intersection of the at least two depressions formed on the upper surface and lower surface forming corresponding ridges.

23. The spinal implant of claim 18, wherein a first slot with a first orientation formed in the in the first lateral portion, a second slot with a second orientation formed in the second lateral portion, and the head portion includes a first post and a second post, the first post being received in the first slot and the second post being received in the second slot, the first orientation and the interaction of the first post in the first slot forcing the upper first end plate portion to pivot as the head portion moves from the first position toward the second position, and the second orientation and the interaction of the second post in the second slot forcing the lower second end plate portion to pivot as the head portion moves from the first position toward the second position.

* * * * *